(12) United States Patent
Hagiwara

(10) Patent No.: US 12,290,408 B2
(45) Date of Patent: May 6, 2025

(54) ELECTRONIC ENDOSCOPE SYSTEM

(71) Applicant: HOYA CORPORATION, Tokyo (JP)

(72) Inventor: Masayuki Hagiwara, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 219 days.

(21) Appl. No.: 17/795,391

(22) PCT Filed: Feb. 3, 2021

(86) PCT No.: PCT/JP2021/004002
§ 371 (c)(1),
(2) Date: Jul. 26, 2022

(87) PCT Pub. No.: WO2021/176939
PCT Pub. Date: Sep. 10, 2021

(65) Prior Publication Data
US 2023/0097283 A1 Mar. 30, 2023

(30) Foreign Application Priority Data
Mar. 5, 2020 (JP) ................................. 2020-038188

(51) Int. Cl.
*A61B 8/00* (2006.01)
*A61B 1/05* (2006.01)
(Continued)

(52) U.S. Cl.
CPC .............. *A61B 8/5269* (2013.01); *A61B 1/05* (2013.01); *A61B 8/12* (2013.01); *A61B 8/4416* (2013.01); *A61B 8/56* (2013.01); *G01S 7/52077* (2013.01)

(58) Field of Classification Search
CPC ...................................................... A61B 1/05
See application file for complete search history.

(56) References Cited

U.S. PATENT DOCUMENTS

2011/0001851 A1   1/2011 Nakamura
2011/0313320 A1*  12/2011 Gewolb ............... A61B 5/4211
                                                    600/586
(Continued)

FOREIGN PATENT DOCUMENTS

JP    H01-223940 A    9/1989
JP    H06-169888 A    6/1994
(Continued)

OTHER PUBLICATIONS

International Search Report issued in International Bureau of WIPO Patent Application No. PCT/JP2021/004002, dated Apr. 6, 2021, along with an English translation thereof.
(Continued)

*Primary Examiner* — Joseph M Santos Rodriguez
(74) *Attorney, Agent, or Firm* — GREENBLUM & BERNSTEIN, P.L.C.

(57) ABSTRACT

An electronic endoscope system includes: an electronic endoscope including, at a distal end portion, an image sensor that captures an image of a living tissue, and an ultrasound probe that applies ultrasonic waves to the living tissue to obtain an echo signal; a captured image processor including an image processing unit that processes an imaging signal output from the image sensor and generates a captured image; and an ultrasonic image processor including an ultrasonic image processing unit that processes the echo signal output from the ultrasound probe and generates an ultrasonic image, a noise detection unit that detects a periodic noise component included in the echo signal and generated at a level equal to or higher than a preset threshold level, and a noise suppression unit that performs processing of suppressing the detected noise component.

16 Claims, 21 Drawing Sheets

(51) Int. Cl.
*A61B 8/12* (2006.01)
*G01S 7/52* (2006.01)

(56) References Cited

U.S. PATENT DOCUMENTS

| | | | |
|---|---|---|---|
| 2012/0041312 A1* | 2/2012 | Nakahira | G06T 5/70 600/443 |
| 2020/0078118 A1* | 3/2020 | Henderson | A61B 34/20 |

FOREIGN PATENT DOCUMENTS

| | | |
|---|---|---|
| JP | 2008-11925 A | 1/2008 |
| JP | 2008-245705 A | 10/2008 |
| JP | 2009-261441 A | 11/2009 |
| JP | 2011-217842 A | 11/2011 |
| JP | 2014-3801 A | 1/2014 |
| JP | 2017-80040 A | 5/2017 |
| JP | 2019-76707 A | 5/2019 |
| WO | 2010/070791 A1 | 6/2010 |

OTHER PUBLICATIONS

Office Action issued in Japanese Patent Application No. 2020-038188, dated Dec. 19, 2023, along with an English translation thereof.
Extended European Search Report issued in EP Application No. 21765030.8, dated Feb. 13, 2024.

* cited by examiner

NOISE

SCAN C
SCAN
SCAN B

HIGH-BRIGHTNESS POINT
FREQUENCY $fn = \dfrac{v}{2x}$ $v$ : SOUND VELOCITY
$x$ : INTERVAL

ELECTRONIC ENDOSCOPE SYSTEM

TECHNICAL FIELD

The present invention relates to an electronic endoscope system that acquires an ultrasonic image.

BACKGROUND ART

An electronic endoscope system is used to observe or treat a living tissue inside a human body. An electronic endoscope system acquires an optical observation image of a subject by using an image sensor as an image of a living tissue. In addition, an endoscopic ultrasonography including an ultrasound probe can obtain an ultrasonic image (ultrasonic tomographic image). A processor connected to an endoscopic ultrasonography functions as an ultrasound diagnostic device and performs inspection and diagnosis. Hereinafter, an endoscope including an image sensor and an ultrasound probe is referred to as an endoscopic ultrasonography (or an electronic endoscope).

An endoscopic ultrasonography includes an image sensor and an ultrasound probe, and an imaging signal transmission line that connects an image sensor provided at a distal end of an insertion portion and a connector connected to a processor is disposed in a flexible pipe extending from the endoscopic ultrasonography to the processor, and an imaging signal is transmitted through the imaging signal transmission line. Further, an ultrasonic signal transmission line connecting the ultrasound probe provided at the distal end of the insertion portion and the connector connected to the processor is disposed in the flexible pipe, and an ultrasonic signal is transmitted through the ultrasonic signal line.

When inspection or diagnosis is performed using ultrasonic waves, power is supplied from the processor to the ultrasound probe, and the ultrasound probe transmits ultrasonic waves to a living tissue and receives reflected waves. The reflected waves received by the ultrasound probe are converted into an echo signal, the echo signal is transmitted to the processor through the ultrasonic signal transmission line, and signal processing is performed on the echo signal by the processor to obtain an ultrasonic image.

The processor includes a switching power supply in addition to a signal processing unit that performs data processing using a signal (an ultrasonic signal or imaging signal) transmitted from the endoscopic ultrasonography, a control unit that controls image display, and the like. The switching power supply generates and supplies a voltage necessary for operating each component device in the endoscopic ultrasonography and the processor. The processor is connected to a monitor for displaying a captured image or ultrasonic image.

In the ultrasonic image obtained based on the echo signal of the ultrasound probe and displayed on the monitor, noise generated in the endoscopic ultrasonography or the processor or noise superimposed on AC power supply and entering from the outside may be mixed as a noise component. The noise component includes, for example, a noise component caused by switching of the switching power supply or a noise component caused by mutual interference between the transmission lines. For example, since the imaging signal transmission line and the ultrasonic signal transmission line are provided close to each other in the flexible pipe, electrostatic coupling or electromagnetic coupling between the transmission lines becomes strong, and a pulse control signal or the like for controlling the image sensor interferes with the ultrasound probe or the ultrasonic signal transmission line, as a result of which a noise component is mixed in the echo signal.

Furthermore, ultrasound-specific noise called artifacts (virtual images that do not actually exist) may also be generated in an ultrasonic image. The echo signal is obtained by receiving an echo caused by reflection of generated ultrasonic waves from the inside of a living body, and a virtual image, that is, an artifact, is generated as noise due to a side lobe artifact, a grating lobe, multiple reflection, and the like. In addition, as high-frequency noise generated by the switching power supply is superimposed on a reception signal of the ultrasonic signal, an artifact may appear in an ultrasonic image generated as an ultrasonic diagnostic image.

For the noise components in an ultrasonic image, JP 2014-003801 A discloses an ultrasonic image processor capable of eliminating periodic noise caused by an operation of a DC/DC converter. A main converter that inputs power from a power input unit and outputs power of a constant voltage, and a plurality of sub-converters that input the power of the constant voltage and outputs power to a circuit included in the ultrasonic image processor are provided, and switching operations of the main converter and the sub-converters are synchronized to reduce spike noise.

JP 2019-076707 A discloses a method of changing a switching frequency of a switching power supply by a preset change width in order to suppress an increase in switching noise appearing in an ultrasonic image. This is because when the switching frequency becomes an integer multiple of a pulse repetition frequency which is a frequency at which an ultrasonic pulse is transmitted when scanning is executed, switching noise caused by switching appears in an ultrasonic image based on ultrasonic image data generated by execution of brightness (B) mode scanning or motion (M) mode scanning.

JP 2017-080040 A discloses a method in which an image generation unit, a detection unit, and a control unit are provided, when the detection unit detects a peculiar change in output from an external device or an ultrasound probe in a time direction, the control unit displays, on the display unit, a reference image including a medical image at substantially the same position as that of an ultrasonic image displayed on the display unit in response to the detection of the peculiar change by the detection unit, and noise is eliminated.

SUMMARY OF INVENTION

Technical Problem

In an electronic endoscope system including an endoscopic ultrasonography and a processor, it is preferable to accurately extract and image an echo signal that is likely to be buried in a noise component, for more accurate diagnosis. Furthermore, further reduction in diameter of a flexible pipe is required in the future in order to reduce a physical burden on a patient having a body cavity into which the endoscopic ultrasonography is inserted. In the ultrasonic signal transmission line and the imaging signal transmission line having a conventional shield structure to suppress noise from entering, the shielding performance is inevitably deteriorated due to the limitation by the shield structure caused by the reduction in diameter, and a noise component is easily generated.

Furthermore, in a case where noise is externally superimposed on the AC power supply that is a power source for driving the endoscopic ultrasonography and the processor, the noise is reduced to some extent by a power supply circuit or a filter circuit. However, in a case where a noise level is high or in a case where EMI noise or the like is superimposed on the echo signal along an unintended route, the noise becomes a noise component of an ultrasonic image, which leads to deterioration in image quality. Moreover, detection of a minute echo signal is also required for high definition, and how to suppress a noise component of an ultrasonic image is a major problem.

An object of the present invention is to provide an electronic endoscope system capable of efficiently detecting a noise component periodically generated in an ultrasonic image, suppressing the noise component, and generating a highly accurate ultrasonic image when acquiring an ultrasonic image using an ultrasound probe.

Solution to Problem

An aspect of the present invention is an electronic endoscope system that acquires an ultrasonic image, the electronic endoscope system including: an electronic endoscope including, at a distal end portion, an image sensor that captures an image of a living tissue, and an ultrasound probe that applies ultrasonic waves to the living tissue to obtain an echo signal; a captured image processor including an image processing unit that processes an imaging signal output from the image sensor and generates a captured image; and an ultrasonic image processor including an ultrasonic image processing unit that processes the echo signal output from the ultrasound probe and generates an ultrasonic image, a noise detection unit that detects a noise component included in the echo signal and periodically generated at a level equal to or higher than a preset threshold level, and a noise suppression unit that performs processing of suppressing the detected noise component.

The noise detection unit may include a cycle length detection unit that calculates a noise cycle in which the noise component is periodically generated and calculates a cycle length from a minimum value and a maximum value of the noise cycle, and the noise detection unit detects the noise component by using the noise cycle and the cycle length.

The noise suppression unit may perform gain change processing of changing an amplification gain value between a pixel value of the detected noise component at a noise pixel position in the ultrasonic image and a pixel other than the noise pixel at the noise pixel position.

The noise suppression unit may include a band elimination filter that obtains a frequency band corresponding to the noise cycle based on the noise cycle and the cycle length and eliminates the noise component from the echo signal by using the frequency band.

The noise suppression unit may perform correction processing of replacing a pixel value of the detected noise component at a noise pixel position in the ultrasonic image with an interpolation pixel value generated based on pixel values of peripheral pixels positioned around the noise pixel position.

The noise suppression unit may change at least one of operation frequencies of a plurality of component devices included in the captured image processor and the ultrasonic image processor so as to be separated from a generation cycle of the noise component periodically generated in the echo signal.

The operation frequency may include at least one of an ultrasonic frequency of the ultrasound probe or an image sensor operation frequency of the image sensor.

The ultrasonic image processor may include, as the component device, an A/D conversion unit that converts the echo signal, which is an analog signal, into a digital signal by sampling, and the operation frequency may include a sampling frequency of the echo signal in the A/D conversion unit.

The ultrasonic image processor may include, as the component device, a DC/DC converter that is a switching power supply for driving the electronic endoscope, the captured image processor, and the ultrasonic image processor, and the operation frequency includes a switching frequency in the DC/DC converter.

The ultrasonic image processor may include, as the component device, an AC/DC converter which is a switching power supply that converts AC power received from an external commercial power supply into DC power and supplies the DC power to the DC/DC converter, and the operation frequency includes a switching frequency in the AC/DC converter.

The DC/DC converter and the AC/DC converter may include a storage battery that supplies DC power, and the noise suppression unit may perform switching from the DC/DC converter and the AC/DC converter to the storage battery when the noise component is detected.

The electronic endoscope system may include an electronic endoscope position measurement device that specifies a position of the electronic endoscope by using magnetism when the electronic endoscope is inserted into a body cavity, the endoscope position measurement device may include a drive unit of a transmission coil wound around the electronic endoscope, and a position specifying unit that specifies the position of the electronic endoscope by using a signal from the transmission coil when the electronic endoscope is inserted into the body cavity, and the noise suppression unit may change an operation frequency of the transmission coil to be generated or stop generation of the magnetism when the noise component is detected.

The noise detection unit may create a noise component inference model that has learned, by machine learning, a presence or absence of the noise component in advance by using, as training data, a training ultrasonic image without the noise component and a training ultrasonic image with the noise component, and determine the presence or absence of the noise component by inputting the ultrasonic image generated by the image processing unit to the noise component inference model.

The noise suppression unit may create a noise control inference model that has learned, by machine learning, a relationship between: operation environment information of the electronic endoscope, the captured image processor, or the ultrasonic image processor and a feature amount of the ultrasonic image; and information regarding whether a countermeasure for suppressing the noise component is effective or ineffective according to the operation environment information, and may set a countermeasure effective for suppressing the noise by extracting the feature amount of the ultrasonic image when the noise component is detected in a newly generated ultrasonic image by the noise detection unit, and inputting, to the created noise control inference model, the operation environment information and the extracted feature amount when the noise component is detected.

The operation environment information may include operation frequencies of a plurality of component devices included in the captured image processor and the ultrasonic image processor, and the operation frequencies may include an ultrasonic frequency of the ultrasound probe and an operation frequency of the image sensor, a sampling frequency of the echo signal in the A/D conversion unit, a switching frequency in the DC/DC converter and the AC/DC converter, and an operation frequency of a transmission coil of the electronic endoscope position measurement device.

Advantageous Effects of Invention

With the above-described electronic endoscope system, it is possible to efficiently detect a noise component periodically generated in an ultrasonic image, suppress the noise component, and generate a highly accurate ultrasonic image when acquiring an ultrasonic image using an ultrasound probe.

DESCRIPTION OF EMBODIMENTS

Overall Configuration of Electronic Endoscope System

Figure 1:
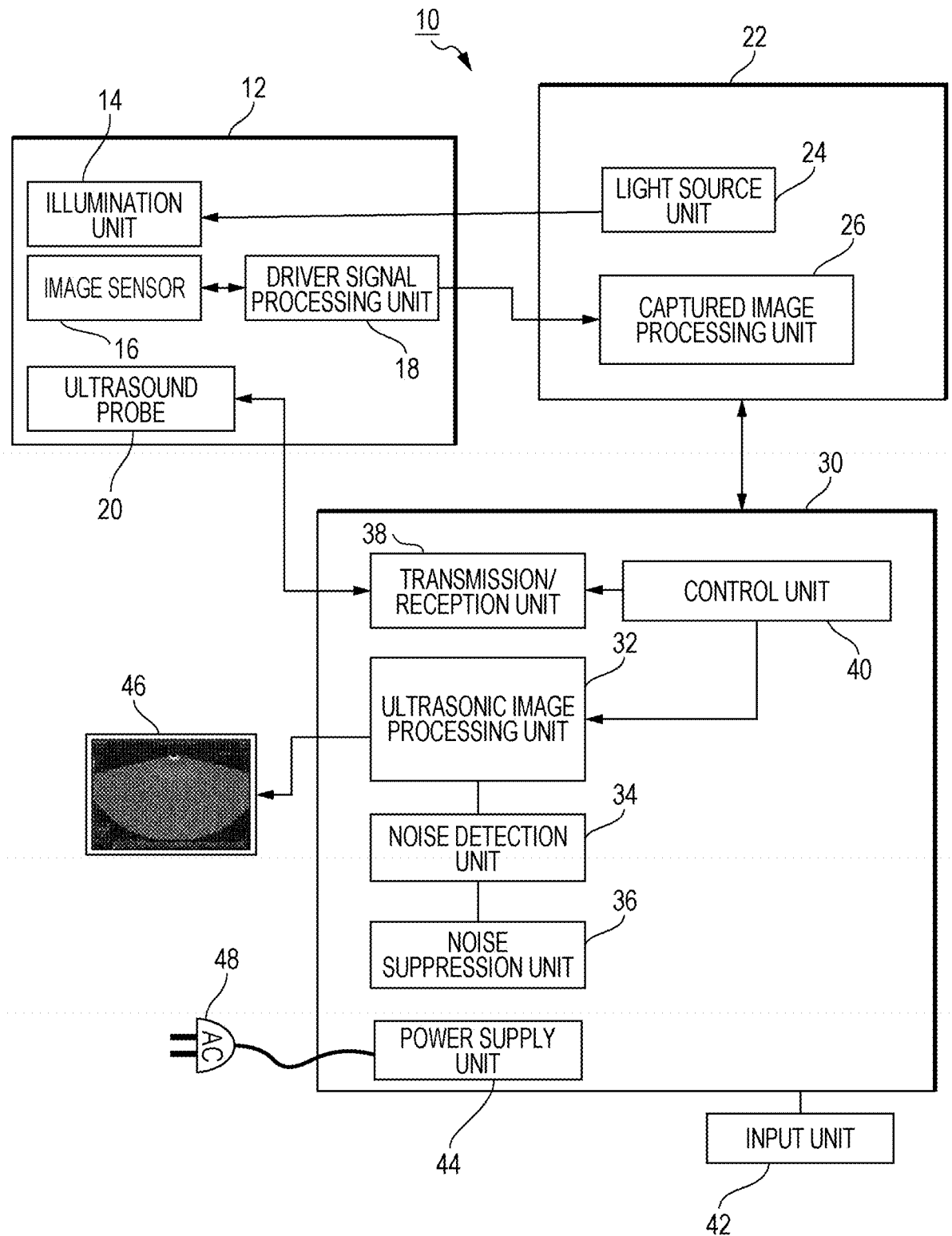
FIG. 1 is a block diagram illustrating an example of an overall configuration of an electronic endoscope system of an embodiment.

FIG. 1 is a block diagram illustrating an overall configuration of an electronic endoscope system of an embodiment. An electronic endoscope system 10 that acquires an ultrasonic image includes an electronic endoscope 12, a captured image processor 22, and an ultrasonic image processor 30.

The electronic endoscope 12 includes an illumination unit 14 that irradiates a living tissue, an image sensor 16 that images a living tissue, a driver signal processing unit 18 that preprocesses a signal captured by the image sensor 16, and an ultrasound probe 20 that applies ultrasonic waves to a living tissue to obtain an echo signal. The ultrasound probe 20 is a phased array type probe capable of acquiring echo signals in various directions by a plurality of probe elements outputting ultrasonic waves at predetermined time intervals, the probe elements being arranged in a predetermined direction.

An image signal of a living tissue is input from the image sensor 16 to the driver signal processing unit 18 at a predetermined frame cycle, and is output to a system controller 102 and the captured image processing unit 26 of the captured image processor 22. The frame cycle is 1/30 seconds or 1/60 seconds, for example.

The driver signal processing unit 18 accesses a memory 92 to read device-specific information of the electronic endoscope 12. The device-specific information of the electronic endoscope 12 recorded in the memory 92 includes, for example, the number of pixels or sensitivity of the image sensor 16, an operable frame rate, A-model number, or the like.

The captured image processor 22 includes a light source unit 24 that transmits a light source to the illumination unit 14, and the captured image processing unit 26 that generates a captured image by processing an imaging signal output from the image sensor 16.

The ultrasonic image processor 30 includes a transmission/reception unit 38 that transmits a drive signal to the ultrasound probe 20 and receives echo waves, an ultrasonic image processing unit 32 that generates an ultrasonic image by processing an echo signal from the ultrasound probe 20, a noise detection unit 34 that detects a noise component included in an echo signal and periodically generated at a level equal to or higher than a preset threshold level, and a noise suppression unit 36 that performs processing of suppressing a detected noise component.

The ultrasonic image processing unit 32 performs predetermined calculation based on a digital echo signal as grayscale image data by, for example, brightness modulation, and generates a one-dimensional B-mode image in one direction. Furthermore, the ultrasonic image processing unit 32 creates one two-dimensional B-mode image by arranging one-dimensional B-mode images in a plurality of directions generated based on echo signals obtained from the phased array type ultrasound probe 20 in a predetermined azimuth direction in accordance with phased array scanning. Furthermore, image processing using known technologies such as gain processing and contrast processing is performed on the created image, and shade processing corresponding to a display range of an image in an ultrasonic image display unit 46 is performed.

The ultrasonic image processor 30 includes a display unit 46 that displays a generated ultrasonic image and has an input function that enables input using a touch panel. The ultrasonic image processor 30 further includes an input unit 42 that operates the ultrasonic image processor 30, a power supply unit 44, and an AC power input unit 48.

The input unit 42 receives inputs of various types of information using a keyboard, a mouse, a touch panel, or the like. The ultrasonic image display unit 46 displays various types of information including a generated ultrasonic image. The power supply unit 44 supplies power for driving the electronic endoscope 12 and the captured image processor 22 in addition to the ultrasonic image processor 30. The power supply unit 44 includes, for example, a DC/DC converter that is a switching power supply as a component device, and generates a DC voltage by a switching frequency in the DC/DC converter. A plurality of DC/DC converters are provided, and each DC/DC converter converts an input DC voltage into a desired DC voltage, and power is supplied to each device.

The noise detection unit 34 detects whether or not an echo signal includes a noise component periodically generated at a level equal to or higher than a preset threshold level. A method of detecting a noise component is not particularly limited, but for example, it is preferable to include a cycle length detection unit that calculates a noise cycle in which a noise component is periodically generated and calculates a cycle length from a minimum value and a maximum value of the noise cycle, and the noise detection unit detects a noise component by using the noise cycle and the cycle length.

The noise detection unit 34 may further perform frequency analysis using fast Fourier transform (FFT) to determine whether or not there is a spectral peak equal to or higher than a set threshold level. Since an echo signal reflected at a boundary surface of a living tissue does not have periodicity, a spectral peak is less likely to exist, and thus, the spectral peak is likely to be a peak of a generated periodically noise component.

The noise suppression unit 36 performs processing for suppressing a detected noise component. The suppression of a noise component includes setting processing of changing an operation of each device of the electronic endoscope system 10 in such a way as to suppress generation of a periodically generated noise component when an echo signal is output by the ultrasound probe 20, and performing interpolation processing on a two-dimensional B-mode image created by the ultrasonic image processing unit 32. The processing of changing the operation of each device and the interpolation processing on the two-dimensional B-mode image will be described later.

Electronic Endoscope

Figure 2:
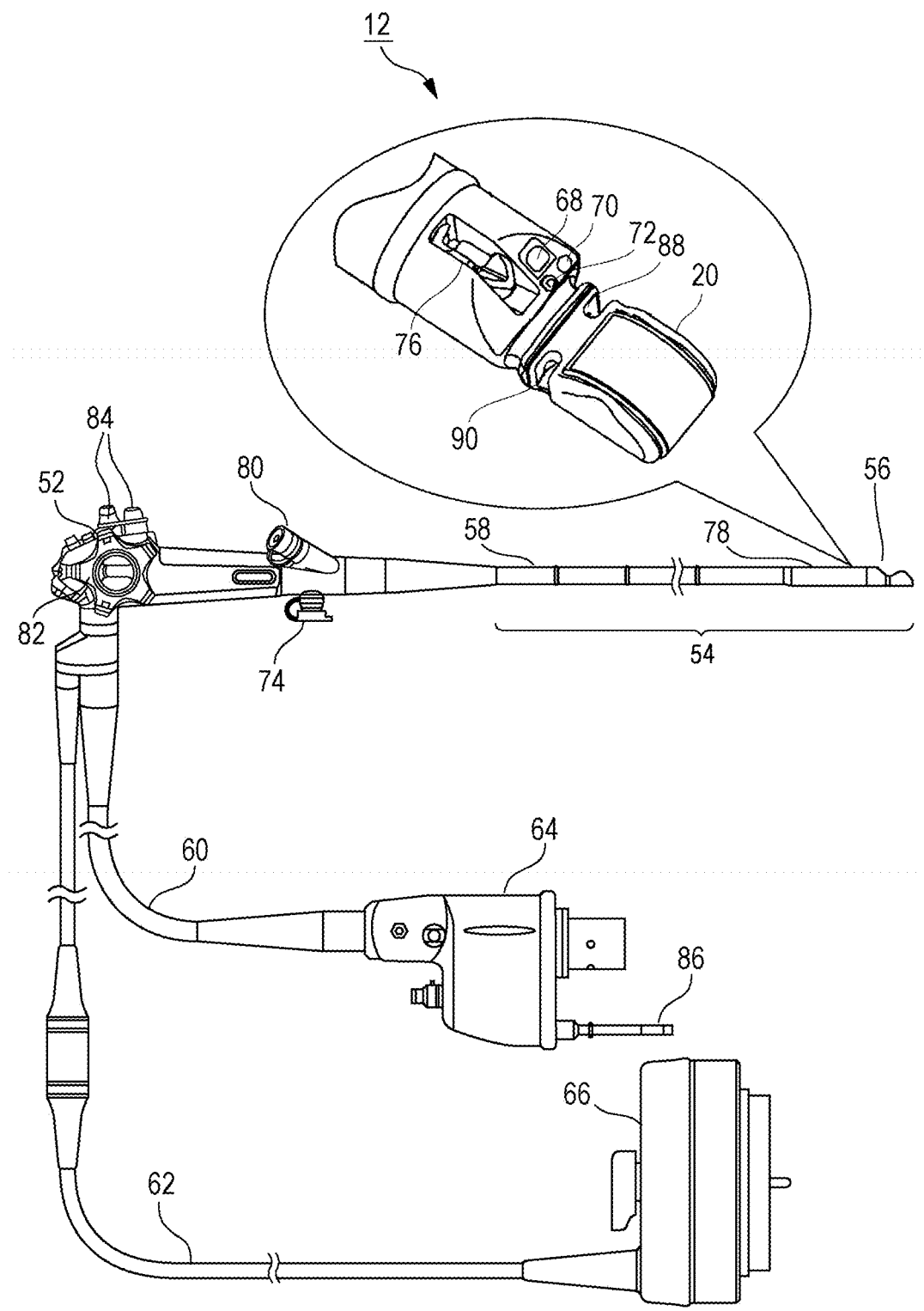
FIG. 2 is a view for describing an example of an electronic endoscope including an ultrasound probe and used in the electronic endoscope system according to an embodiment.

FIG. 2 is a view for describing an example of the electronic endoscope including the ultrasound probe and used in the electronic endoscope system according to an embodiment.

The electronic endoscope 12 includes an operation unit 52, an insertion portion 54 including a distal end portion 56 and a soft portion 58 mainly provided inside, a flexible cable 60 including a light guide cable inside, a scanner connector cable 62, a connector 64, and a scanner connector 66.

The distal end portion 56 is a sensor that inspects a living tissue, and includes an image sensor unit 68, an emission end surface 70, and the ultrasound probe 20. The ultrasound probe 20 includes a transducer array in which a plurality of ultrasonic transducers, for example, piezoelectric elements, are arrayed as probe elements. Each of these transducers transmits ultrasonic waves according to a drive signal, receives reflected waves from a subject, and outputs an analog reception signal. Each of the transducers is configured using, for example, an element in which electrodes are formed at both ends of a piezoelectric body formed of lead zirconate titanate (PZT) which is a piezoelectric ceramic or poly vinylidene difluoride (PVDF) which is a polymer piezoelectric element.

The image sensor unit 68 of the distal end portion 56 is provided with an objective lens and the image sensor 16. The objective lens forms an image of light returning from a living tissue irradiated with illumination light on a light receiving surface of the image sensor 16. The image sensor 16 is a single-plate color Charge Coupled Device (CCD) image sensor having a Bayer pixel arrangement. The single-plate color CCD image sensor accumulates an optical image formed by each of pixels on the light receiving surface, as charges corresponding to the amount of light, and generates and outputs image signals corresponding to color components, Red (R), Green (G), and Blue (B). The image sensor 16 is not limited to a CCD image sensor, and a Complementary Metal Oxide Semiconductor (CMOS) image sensor or other types of imaging devices can also be used. The image sensor 16 may include a complementary color filter.

Incident illumination light is emitted from an emission end surface 70 at the distal end portion 56 through a light distribution lens. The illumination light is incident on the illumination unit 14 of the electronic endoscope 12 via a light guide 94.

An outer portion of the distal end portion 56 is formed of a hard resin. The image sensor unit 68 is provided with the image sensor 16, an objective lens, an illumination lens, and the like (not illustrated) for imaging performed by the image sensor 16.

The distal end portion 56 further includes an air/water supply nozzle 72 that discharges or sucks liquid or gas. The air/water supply nozzle 72 discharges liquid such as water for cleaning the surfaces of the objective lens and the illumination lens attached to the image sensor 16, and discharges gas such as air for eliminating liquid and foreign matters remaining on the surfaces of the objective lens and the illumination lens. In addition, a balloon (not illustrated) used for performing ultrasonic diagnosis by being filled with liquid and brought into contact with a living tissue is attached to the distal end portion 56, and the distal end portion 56 is provided with a balloon water injection port 88 and a balloon water suction port 90. Furthermore, the distal end portion 56 is provided with a forceps elevator 76 for bringing a flexible puncture needle (not illustrated) into contact with a living tissue, and is also provided with an opening for sucking liquid or gas on a living tissue through the forceps elevator 76.

The insertion portion 54 has a bending section 78 that is bent in a vertical direction and a horizontal direction. A portion that is more adjacent to a proximal end side (a side adjacent to the operation unit 52) than the bending section 78 is is the flexible soft portion 58 that can be bent by its own weight or an operation by an operator.

The soft portion 58 is provided between the bending section 78 and the operation unit 52, and a signal line of a sensor provided at the distal end portion 56 and a plurality of individual flow paths through which gas or fluid flows from the opening are provided in the soft portion 58. These individual flow paths are formed by pipes, tubes, or long holes.

A flexible treatment tool insertion port protrusion 80 for inserting a puncture needle and a forceps elevation wire cleaning port 74 protrude adjacent to the operation unit 52 and the distal end portion 56. A cap is detachably attached to an opening of an end portion of the treatment tool insertion port protrusion 80. A flexible treatment tool insertion/suction pipe extending from the treatment tool insertion port protrusion 80 toward the distal end portion 56 is provided inside the insertion portion 54. The treatment tool insertion/suction pipe is opened by the forceps elevator 76. A puncture needle inserted into the treatment tool insertion/suction pipe from the treatment tool insertion port protrusion 80 can protrude outward from an opening of a distal end of the treatment tool insertion/suction pipe in the forceps elevator 76 and is used to palpate a living tissue.

The operation unit 52 includes a plurality of operation buttons 84 of a flow path switching switch, and a common flow path through which fluid flows and which extends from the connector 64 in the flexible cable 60 is provided in the operation unit 52. A bending operation lever 82 is a lever operated by an operator to bend the bending section 78 in the vertical direction and the horizontal direction. The bending section 78 is bent in the vertical direction and the horizontal direction according to a rotation operation of the bending operation lever 82.

The flexible cable 60 connects the connector 64 connected to the captured image processor 22 and the operation unit 52. The connector 64 is also provided with an opening port of the common flow path for supplying or sucking fluid.

The connector 64 includes a light source insertion portion 86 and is connected to the captured image processor 22. Illumination light generated by a light source unit in the captured image processor 22 is transmitted from the connector 64 toward the distal end portion 56 through the inside of the flexible cable 60, the operation unit 52, and the light guide cable in the insertion portion 54. Further, from the connector 64, a drive signal is transmitted from the captured image processor 22 to the image sensor 16 via a signal line in the flexible cable 60. An image signal captured by the image sensor 16 is transmitted to the captured image processor 22 via the flexible cable 60, the operation unit 52, and a signal line in the insertion portion 54.

The scanner connector 66 is connected to the ultrasonic image processor 30 and transmits an echo signal scanned by the ultrasound probe 20 to the ultrasonic image processing unit 32 via the scanner connector cable 62. The ultrasonic image processing unit 32 processes the echo signal to generate a diagnostic image of a living tissue of an inspection target, and displays the generated image on the display unit 46. Further, the scanner connector cable 62 transmits a drive signal of the ultrasound probe 20 from the ultrasonic image processor 30 to a piezoelectric element of the ultrasound probe 20. The piezoelectric element can convert electrical energy into mechanical energy, and generates ultrasonic waves by expansion and contraction due to a voltage change.

The connector 64 is connected to the driver signal processing unit 18. An image signal of a living tissue is input from the image sensor 16 to the driver signal processing unit 18 at a predetermined frame cycle, and is output to the system controller and the captured image processing unit 26 of the captured image processor 22. The frame cycle is 1/30 seconds or 1/60 seconds, for example.

Processor for Electronic Endoscope

Figure 3:
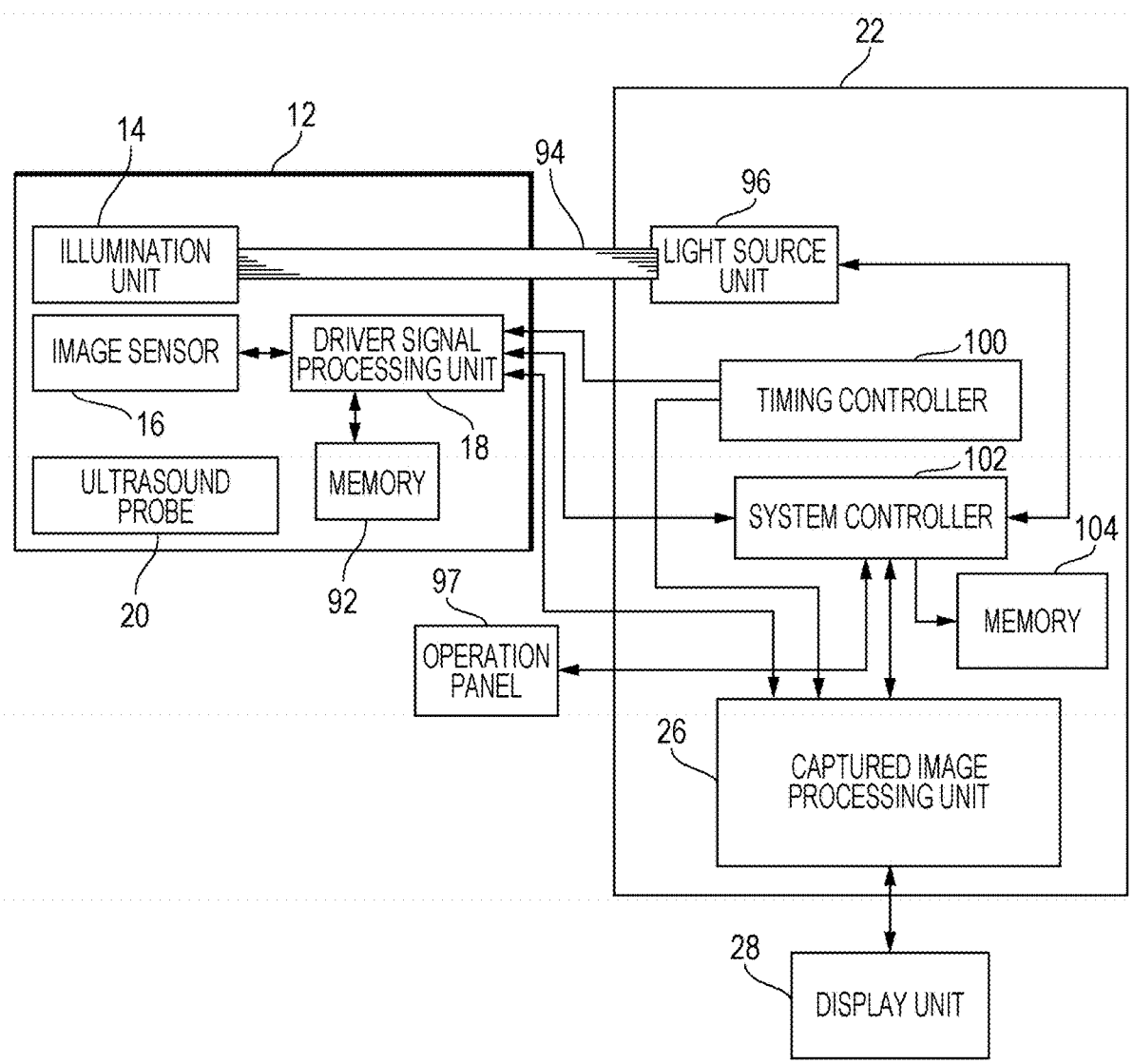
FIG. 3 is a block diagram illustrating an example of schematic configurations of the electronic endoscope and a captured image processor used in the electronic endoscope system according to an embodiment.

FIG. 3 is a block diagram illustrating an example of schematic configurations of the electronic endoscope and the captured image processor used in the electronic endoscope system according to an embodiment. The captured image processor 22 includes the system controller 102 and a timing controller 100 for control. The system controller 102 executes various programs stored in a memory 104 and integrally controls the entire electronic endoscope system 10. The system controller 102 is connected to an operation panel 97.

The system controller 102 changes each operation of the electronic endoscope system 10 and a parameter for each operation in accordance with an operator's instruction input from the operation panel 97. The input operator's instruction includes an instruction to switch an operation mode of the electronic endoscope system 10 and the like. According to an embodiment, there are a normal mode and a special mode as the operation modes. The timing controller 100 outputs a clock pulse for adjusting an operation timing of each unit to each portion in the electronic endoscope system 10.

A light source unit 96 transmits illumination light to the illumination unit 14 of the electronic endoscope 12 through the light guide 94. Examples of the light source include a high-brightness lamp such as a xenon lamp, a halogen lamp, a mercury lamp, or a metal halide lamp. The illumination light transmitted from the light source is condensed by a condensing lens (not illustrated) and is limited to an appropriate amount of light by an aperture. A motor is mechanically connected to the aperture via a transmission mechanism such as an arm or a gear (not illustrated). An opening degree of the aperture can be changed in order to make the brightness of a video displayed on a display screen of a captured image display unit 28 appropriate.

The illumination light having passed through the aperture is incident on the illumination unit 14 of the electronic endoscope 12 via the light guide 94. The incident illumination light is emitted from the emission end surface 70 at the distal end portion 56 through the light distribution lens.

As a light source of the light source unit 96, a semiconductor light emitting element such as a light emitting diode or a laser diode that emits light in a predetermined wavelength region may be used instead of a white light source that emits white light.

The system controller 102 performs various calculations based on the device-specific information of the electronic endoscope 12 and generates a control signal. The system controller 102 controls an operation and timing of various circuits in the captured image processor 22 in such a way as to perform processing suitable for the electronic endoscope 12 connected to the captured image processor 22. The system controller 102 acquires device-specific information of the memory 92 read by the driver signal processing unit 18.

The timing controller 100 supplies a clock pulse to the driver signal processing unit 18 in accordance with timing control performed by the system controller 102. The driver signal processing unit 18 performs driving control on the image sensor 16 at a timing synchronized with a frame rate of a video processed on the captured image processor 22 side in accordance with the clock pulse supplied from the timing controller 100.

The captured image processor 22 includes the captured image processing unit 26. The system controller 102 reads and executes a program recorded in the memory 104, whereby the captured image processing unit 26 exerts its function. Therefore, the captured image processing unit 26 functions integrally with the system controller 102 and may thus be provided in the system controller 102.

The captured image processing unit 26 is provided with a pre-stage signal processing circuit, and performs demosaic processing on each image signal of R, G, and B input from the driver signal processing unit 18 at a frame cycle. Specifically, interpolation processing by peripheral pixels of G and B is performed on each image signal of R, interpolation processing by peripheral pixels of R and B is performed on each image signal of G, and interpolation processing by peripheral pixels of R and G is performed on each image signal of B. As a result, all the image signals are converted into image data having information of three color components of R, G, and B. Further, the pre-stage signal processing circuit performs known processing such as color correction, matrix calculation, and white balance correction.

The captured image processing unit 26 may include a post-stage signal processing circuit. The post-stage signal processing circuit performs predetermined signal processing on the image data to generate moving image data, and converts the moving image data into a predetermined video format signal. The video format signal obtained by conversion is used for displaying a moving image on the display unit 46. As a result, a moving image of a living tissue is displayed on the display screen.

Imaging Mode of Ultrasonic Image Processor

Imaging modes of the ultrasonic image processor 30 include at least an A-mode and a B-mode. The A-mode is A-mode in which amplitude information of an echo signal in a predetermined direction in a subject is displayed on a time axis. The B-mode is A-mode in which a one-dimensional image or a two-dimensional image in a predetermined direction representing the shape of a tissue in a subject is generated and displayed.

Figure 4:
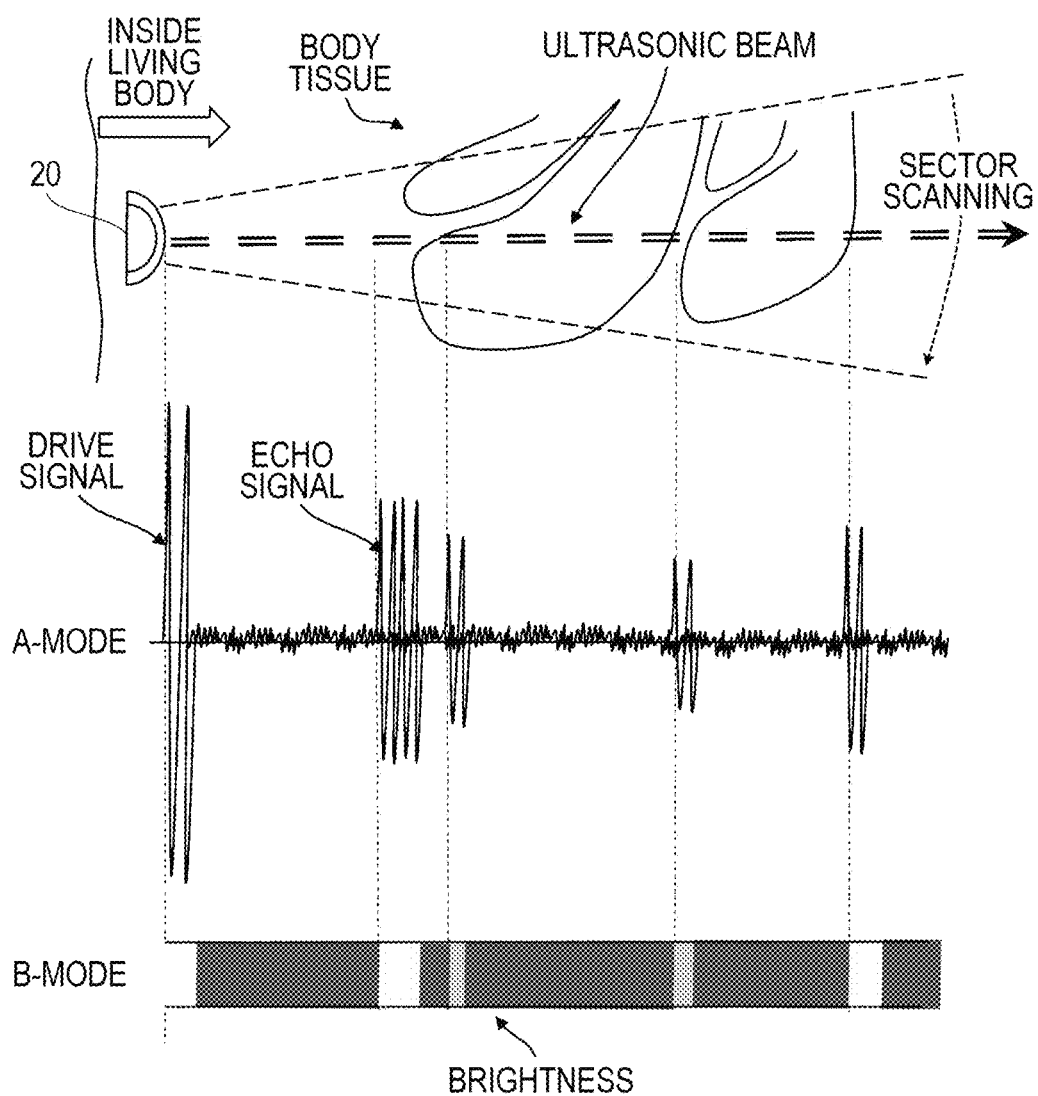
FIG. 4 is a diagram for describing an image forming principle for an ultrasonic image in the electronic endoscope system according to an embodiment.

FIG. 4 is a diagram for describing an image forming principle for an ultrasonic image in the electronic endoscope system according to an embodiment. Image forming using ultrasonic waves is based on an ultrasonic pulse reflection method. FIG. 4 illustrates a state in which an ultrasonic beam is generated from the ultrasound probe 20 in a living body. As the ultrasonic beam, for example, ultrasonic waves of around 10 MHz are emitted in a pulse form into the living body from the ultrasound probe 20. The emitted ultrasonic waves become reflected waves due to a difference in acoustic impedance of a body tissue in the living body, and are received again by the ultrasound probe 20. The reflected waves become an echo signal.

Scanning of the ultrasonic beam in the electronic endoscope 12 is sector scanning by a phased array method, and an echo signal in a predetermined direction can be obtained by the sector scanning. FIG. 4 illustrates an example of an echo signal displayed in the A-mode. In the A-mode, a horizontal axis represents time, a vertical axis represents reflection intensity (amplitude), and an echo signal is displayed. Time represents a biological depth and is a distance between body tissues.

The B-mode is A-mode in which a waveform of the echo signal of the A-mode is subjected to brightness modulation according to the reflection intensity to be converted into brightness, and a tomographic image is represented as a grayscale image by the brightness as illustrated in FIG. 4. The imaging modes of the ultrasonic image processor 30 may further include a known M-mode and a Doppler mode.

Figure 5:
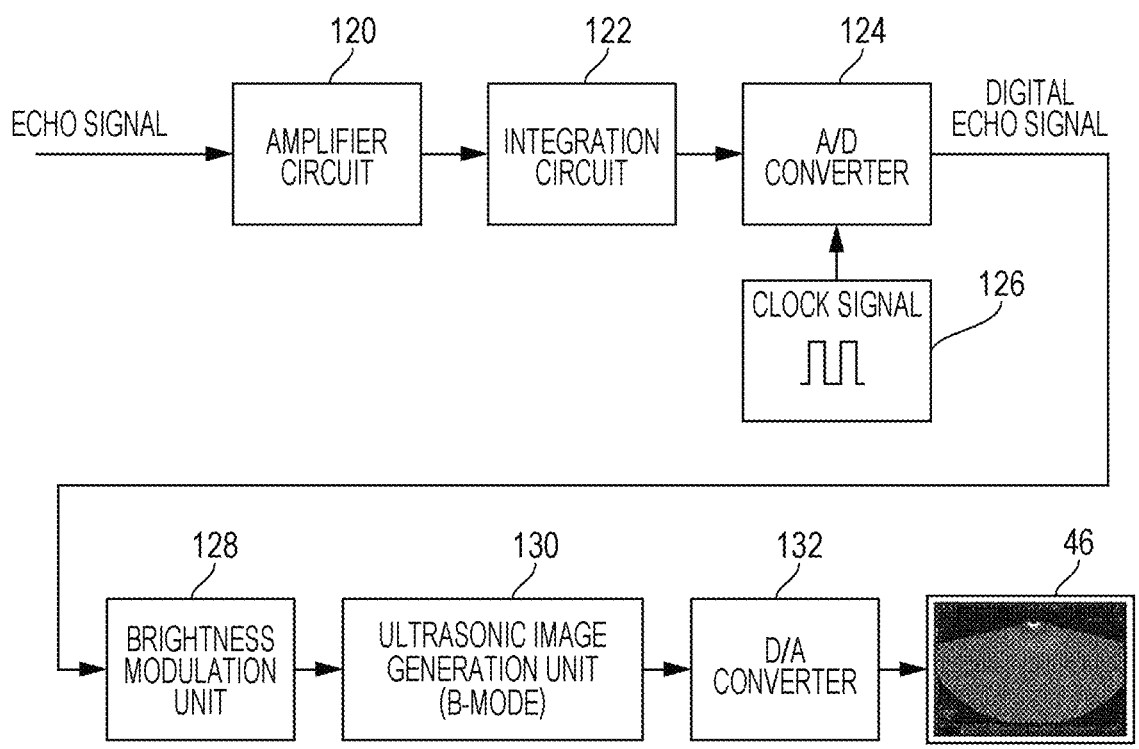
FIG. 5 is a diagram for describing an example of signal processing until an echo signal when acquiring an ultrasonic image is displayed as a B-mode ultrasonic image.

FIG. 5 is a diagram for describing an example of signal processing until an echo signal when acquiring an ultrasonic image is displayed as a B-mode ultrasonic image, which is conventionally used. An echo signal obtained by the ultrasound probe 20 is amplified by an amplifier circuit 120 and integrated by an integration circuit 122 to eliminate harmonic noise. The amplifier circuit 120 and the integration circuit 122 may have an amplification function and a low-pass filter function by an integrated inverting amplification type integration circuit. Next, the echo signal, which is an analog signal, is digitized by an A/D converter 124 at a sampling cycle based on a clock signal 126 to become a digital echo signal.

The digital echo signal is subjected to brightness modulation according to the reflection intensity by a brightness modulation unit 128 and converted into brightness. The digital echo signal converted into brightness is subjected to image processing in an ultrasonic image generation unit 130 and becomes a two-dimensional B-mode tomographic image. This digital image signal is converted into an analog signal by a D/A converter 132 and is displayed as a B-mode tomographic image on the ultrasonic image display unit 46.

Figure 6:
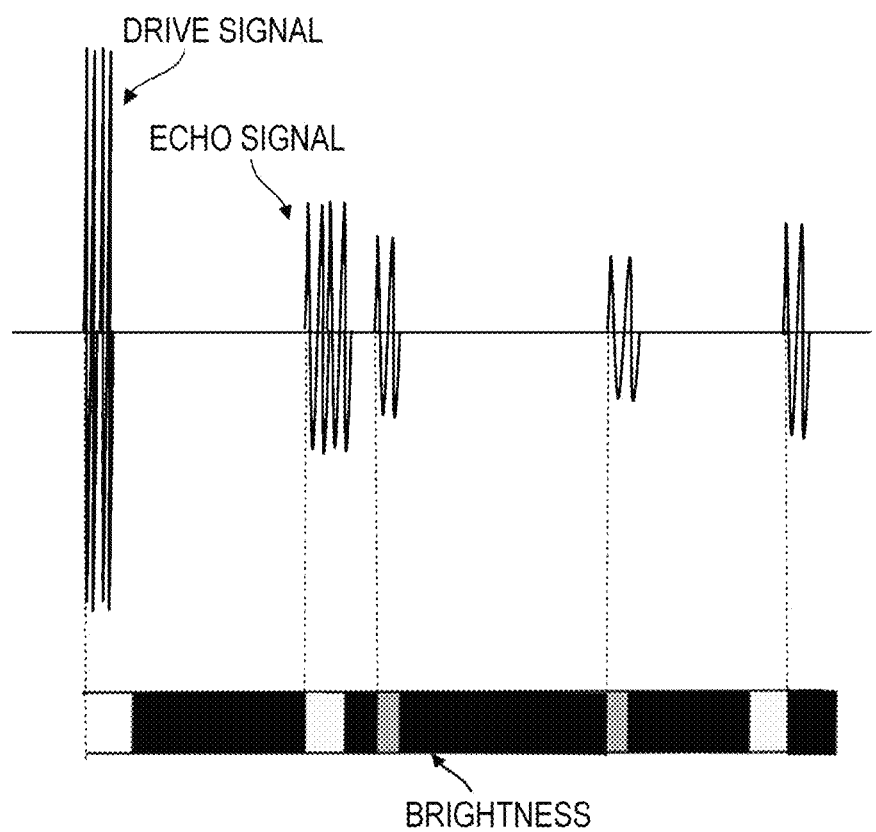
FIG. 6 is a diagram illustrating an example of an echo signal after the echo signal of an A-mode illustrated in FIG. 5 passes through an amplifier circuit and an integration circuit, and a modulated brightness.

FIG. 6 is a diagram illustrating an example of an echo signal and a brightness signal after the echo signal of the A-mode illustrated in FIG. 4 passes through the amplifier circuit 120 and the integration circuit 122. As illustrated in FIG. 6, high-frequency noise is eliminated from the echo signal of the A-mode illustrated in FIG. 4. As illustrated in FIG. 6, the echo signal of the A-mode is a brightness signal from which high-frequency noise has been eliminated. As described above, the conventional noise processing for an ultrasonic image is basically performed by the amplifier circuit 120 and the integration circuit 122 illustrated in FIG. 5 or an inverting amplifier circuit integrated with the amplifier circuit 120 and the integration circuit 122. Note that a frequency corresponding to ½ or more of a sampling frequency of the clock signal 126 of the A/D converter 124 is a frequency that is not digitized by sampling, and the A/D converter 124 also serves as a kind of low-pass filter.

Periodically Generated Noise Component

Figure 7:
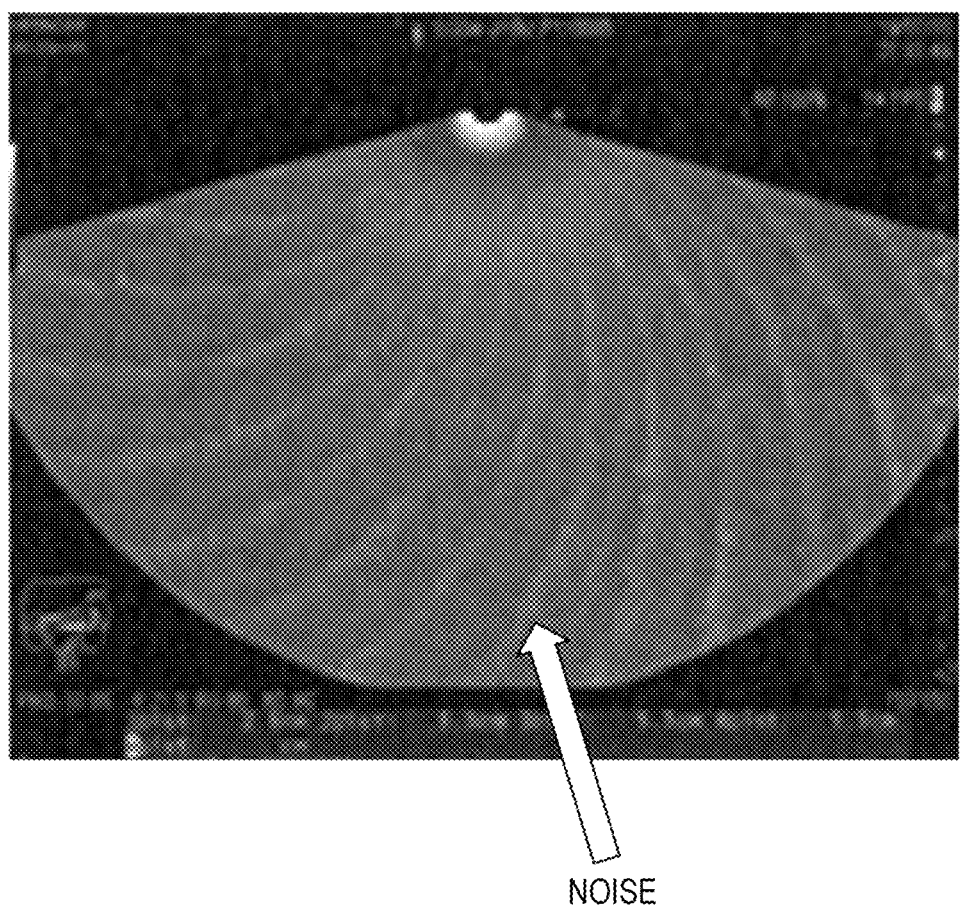
FIG. 7 is a view illustrating an example of a B-mode ultrasonic image obtained by the electronic endoscope system of an embodiment.

FIG. 7 is a view illustrating an example of a B-mode ultrasonic image obtained by the electronic endoscope system of an embodiment. A fan-shaped portion obtained by the sector scanning is an ultrasonic image, and an upper white portion corresponds to a drive signal of the ultrasound probe 20. In this example, radially extending white curves appear as indicated by an arrow. The curves are noise components having a cycle (strictly speaking, a cycle varying within a certain range).

Figure 8:
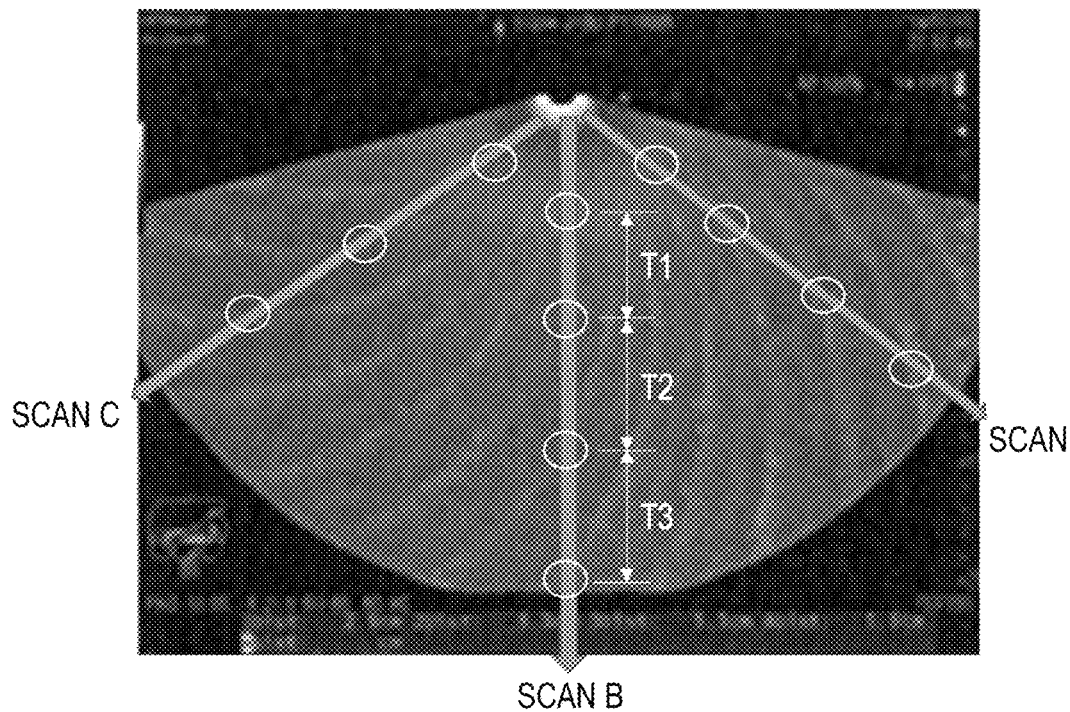
FIG. 8 is a view illustrating an example of a scanning position of an ultrasonic beam and a noise component generation portion in a B-mode ultrasonic image obtained by the electronic endoscope system of an embodiment.

FIG. 8 is a view illustrating an example of a scanning position of an ultrasonic beam and a noise component generation portion in a B-mode ultrasonic image obtained by the electronic endoscope system of an embodiment. Portions where noise is generated in a scan A, a scan B, and a scan C having different scanning positions are indicated by circle marks. For example, noise is generated at four positions in the scan B, and in a case where time intervals between the positions are T1, T2, and T3, T1, T2, and T3 have certain lengths. The time intervals T1, T2, and T3 are not constant, but are time intervals within a certain range.

Furthermore, it can be seen that time intervals in noise generation in the scan A and the scan C are also not constant and are within a certain range, similarly to the scan B. Therefore, a noise component appearing as a radial curve has a cycle length within a certain range in scanning. That is, it is considered as a periodic noise component periodically generated in a certain frequency band in the frequency domain.

Figure 9:
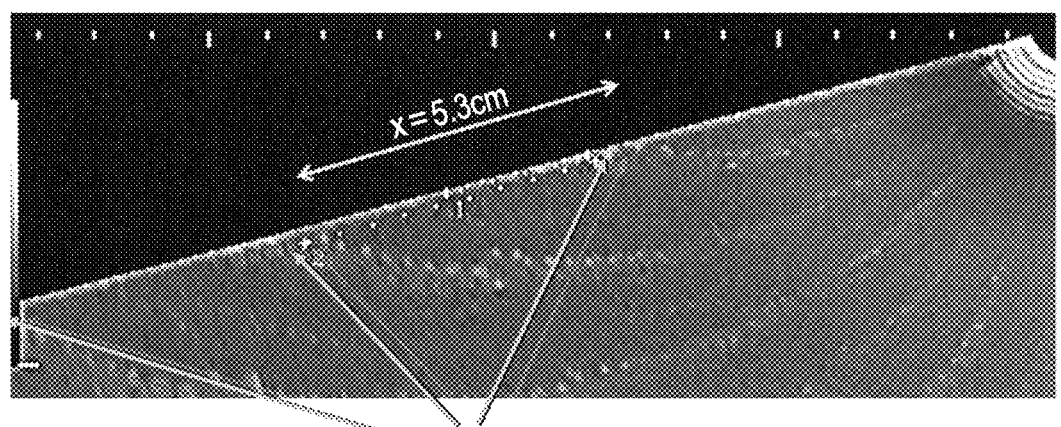
FIG. 9 is a view for describing an example of a generation frequency of a noise component appearing in a B-mode ultrasonic image obtained by the electronic endoscope system of an embodiment.

FIG. 9 is a view for describing an example of a generation frequency of a noise component appearing in a B-mode ultrasonic image obtained by the electronic endoscope system of an embodiment. A measured interval x between high-brightness points representing noise components is 5.3 cm. A noise frequency fn can be expressed by fn=v/2x, in which v is a sound velocity in a living body. In a case where the sound velocity v is, for example, 1540 m/s, the generation frequency fn of the noise component is 14.5 kHz. This frequency becomes a pass band of a frequency characteristic of the low-pass filter in the integration circuit 122 or the inverting amplification type integration circuit, and cannot be handled by the conventional noise processing. Note that the sound velocity depends on a living tissue, and is, for example, 1570 m/s for blood, 1450 m/s for fat, 1560 m/s for kidney, and 1590 m/s for muscle. The average sound velocity is 1540 m/s.

Figure 10:
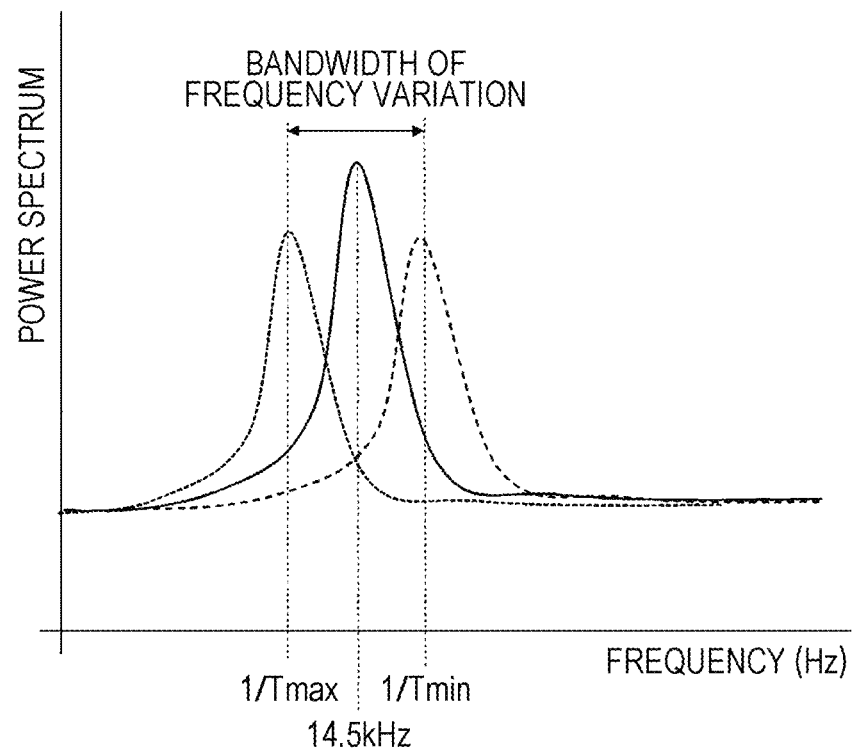
FIG. 10 is a diagram schematically illustrating an example of a power spectrum of a periodic noise component appearing in an ultrasonic image obtained by the electronic endoscope system of an embodiment.

FIG. 10 is a diagram schematically illustrating an example of a power spectrum of a periodic noise component appearing in an ultrasonic image obtained by the electronic endoscope system of an embodiment. A generation cycle of the noise component is not constant, and fluctuates with a cycle length in a certain range, and a peak position of the power spectrum in the frequency domain also fluctuates within a certain bandwidth. The power spectrum varies between the minimum frequency 1/Tmax and the maximum frequency 1/Tmin as illustrated in FIG. 10, in which the minimum cycle of the measured noise component is Tmin and the maximum cycle is Tmax.

The noise frequency fn of the ultrasonic image illustrated in FIG. 7 as a periodically generated noise component has a value of 14.5 kHz calculated as an example. This frequency is considerably lower than several MHz for a signal used in the electronic endoscope 12 or the ultrasonic image processor 30 and several hundred KHz or more of a switching frequency of a switching power supply.

Such a periodically generated noise component is considered to be caused by the following generation factors.

(1) A noise component generated by synchronization of frequencies of clock signals used by a plurality of component devices or frequencies corresponding to integer multiples of frequencies of switching signals of a plurality of component devices (2) A noise component generated by the switching power supply (3) A noise component generated by the electronic endoscope insertion portion 54

About (1)

For example, a case will be considered in which the ultrasonic image processor 30 sets a pulse repetition frequency (PRF) of the drive signal of the ultrasound probe 20 to be an integer multiple of the switching frequency of the switching power supply and performs synchronization to generate a two-dimensional B-mode image. In a case where ultrasonic waves are output in a state in which the switching frequency is approximately an integer multiple of the PRF, there is a possibility that an artifact occurs in a B-mode image.

When transmission and reception are performed between the ultrasound probe 20 and the ultrasonic image processor 30 with the switching frequency set to approximately an integer multiple of the PRF, switching of the switching power supply is performed within a time for detecting an echo signal. Therefore, a noise component derived from switching is generated in each echo signal. In a case where a plurality of echo signals obtained from the same ultrasonic beam are added, a noise component caused by switching generated in each echo signal is added. Therefore, noise components caused by switching are also added according to the number of echo signals to be added, and this becomes a high brightness signal by brightness modulation and becomes noise components periodically generated in a B-mode image.

About (2)

The switching power supply, for example, a step-down DC/DC converter uses, for example, a metal-oxide-semiconductor field-effect transistor (MOSFET) as a switching element. When the MOSFET is turned on/off, resonance occurs in the loop of the converter due to parasitic inductance and parasitic capacitance as parasitic elements, high-frequency noise is generated, and a noise component is applied to an output of the DC/DC converter via a stray capacitance of an output inductor of the step-down DC/DC converter.

The switching power supply such as a DC/DC converter is provided with a surge absorbing element and a snubber circuit for the purpose of suppressing a surge/ringing voltage as a noise component. However, even if such a noise control measure is taken, it is difficult to completely eliminate the noise component, and even if the switching frequency is changed, only the generation timing (cycle) of the noise component is changed, and the noise component is not eliminated. Therefore, it is preferable to change the switching frequency from the viewpoint of preventing a phenomenon in which noise components from a plurality of switching power supplies are synchronized and superimposed.

Figure 11:
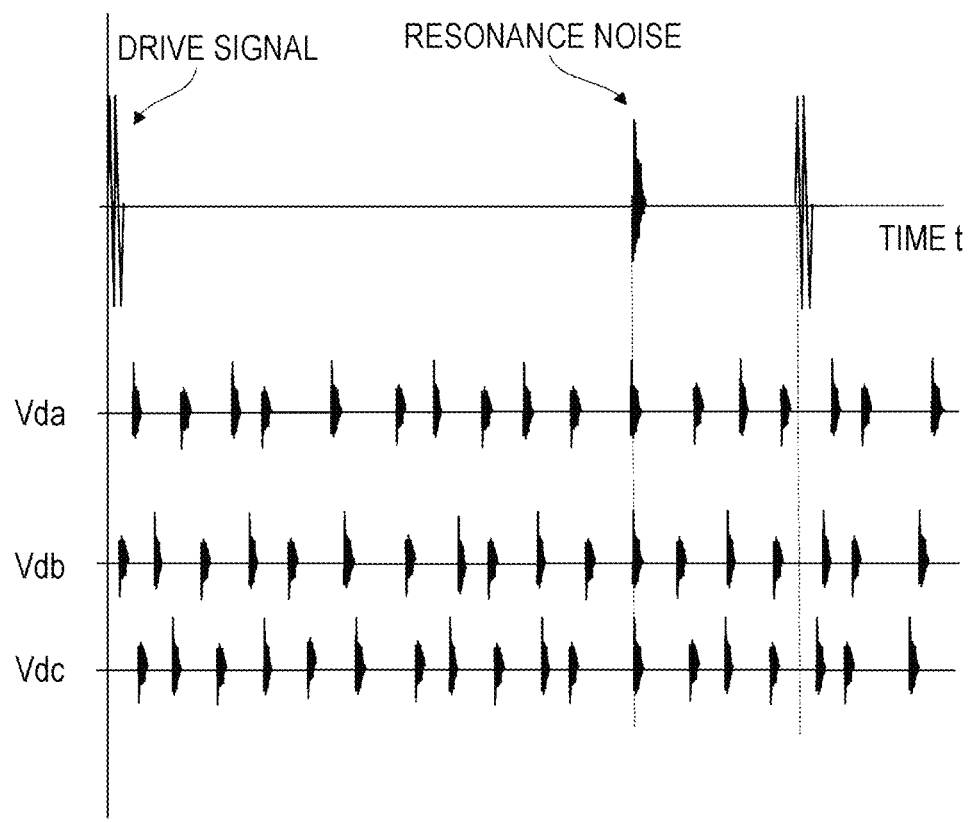
FIG. 11 is a diagram illustrating an example in which noises of a plurality of switching power supplies used in the electronic endoscope system of an embodiment are superimposed on an echo signal.

FIG. 11 is a diagram illustrating an example in which noises of a plurality of switching power supplies used in the electronic endoscope system of an embodiment are superimposed on an echo signal. FIG. 11 is a diagram illustrating an example in which noise components of a plurality of switching power supplies are superimposed on an echo signal. For example, noise components superimposed on DC outputs Vda, Vdb, and Vdc of three switching power supplies become resonance noise components in synchronization at a certain timing, and are superimposed on an echo signal. The resonance noise component may be periodically generated by setting of the switching frequency. In this case, the resonance noise component becomes a noise component periodically generated in a B-mode image.

About (3)

Figure 12:
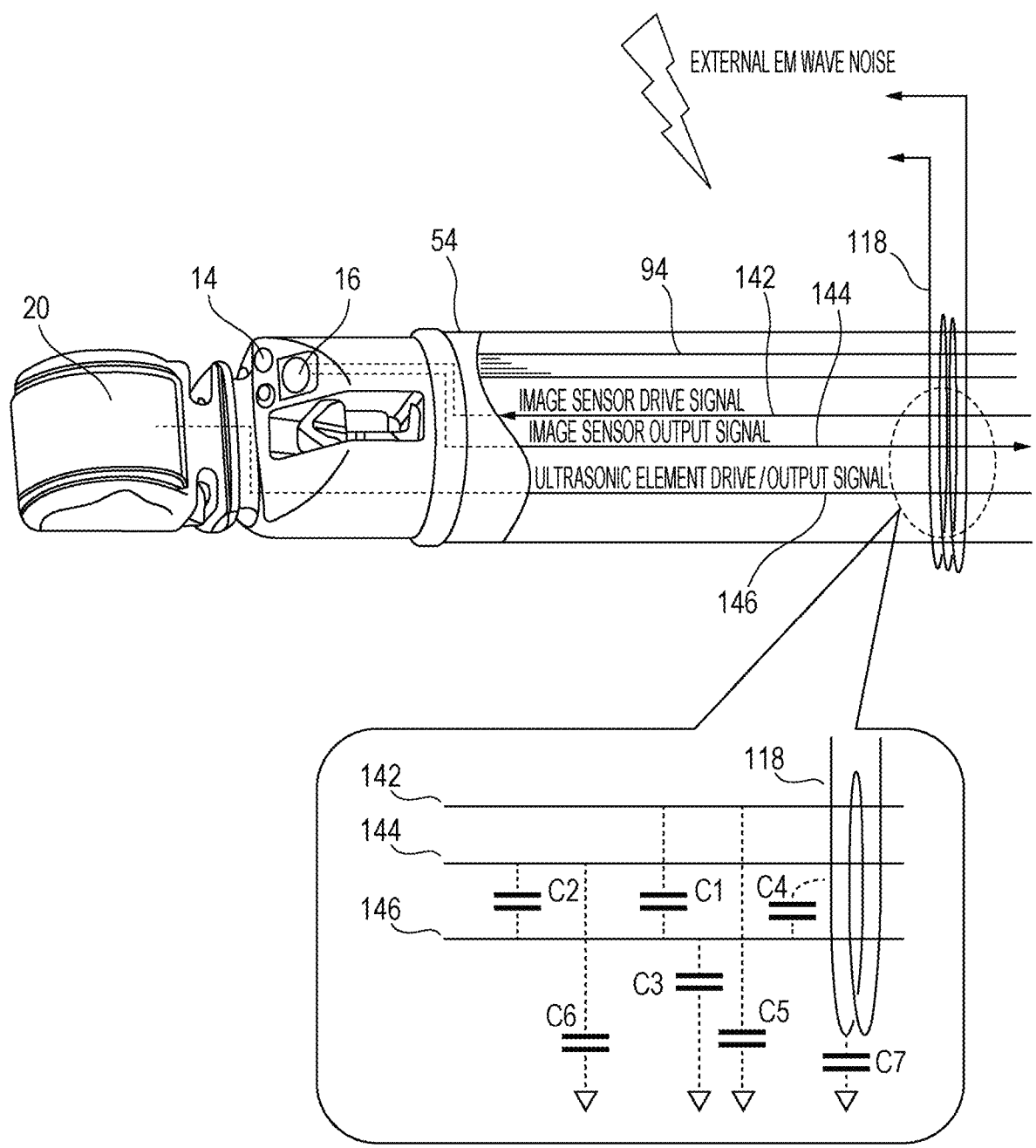
FIG. 12 is a diagram for describing an example of a noise factor at an insertion portion of the electronic endoscope used in the electronic endoscope system of an embodiment.

FIG. 12 is a diagram for describing an example of a noise factor at the insertion portion of the electronic endoscope used in the electronic endoscope system of an embodiment. As described above, the illumination unit 14, the image sensor 16, and the ultrasound probe 20 are provided at the distal end of the insertion portion 54. Light is transmitted to the illumination unit 14 by the light guide 94. An image sensor drive signal line 142 and an image sensor output signal line 144 are connected to the image sensor 16. The ultrasound probe 20 is connected to an ultrasonic element drive/output signal line 146 through which a drive signal and an output signal of an ultrasonic element are transmitted. In addition, a transmission coil 118 of an electronic endoscope position measurement device 110 described later is wound around the insertion portion 54 as necessary.

A stray capacitance exists between the signal line and the transmission coil 118, and noise is induced in the ultrasonic element drive/output signal line 146 by electrostatic coupling. A stray capacitance C1 is a stray capacitance between the image sensor drive signal line 142 and the ultrasonic element drive/output signal line 146. A stray capacitance C2 is a stray capacitance between the image sensor output signal line 144 and the ultrasonic element drive/output signal line 146. A stray capacitance C3 is a stray capacitance between the ultrasonic element drive/output signal line 146 and the earth. A stray capacitance C4 is a stray capacitance between the ultrasonic element drive/output signal line and the transmission coil 118. Further, stray capacitances C5, C6, and C7 are stray capacitances between the earth and the image sensor drive signal line 142, the image sensor output signal line 144, and the transmission coil 118.

Due to the stray capacitances, the ultrasonic element drive/output signal line 146 is electrostatically coupled to each line, and a current flowing as a signal of each line is superimposed on the ultrasonic element drive/output signal line 146 as a noise component in a differential mode. Furthermore, the stray capacitances C5 to C7 generated between the respective signal lines and the earth become noise components in a common mode by electrostatic coupling, and a current flows and is superimposed on the ultrasonic element drive/output signal line 146.

In addition, a magnetic field of the transmission coil 118 and external EM wave noise are also superimposed on the ultrasonic element drive/output signal line 146. Furthermore, as illustrated in FIG. 6, there is a possibility that the clock signal 126 of the A/D converter 124 that digitizes an echo signal is also superimposed on the ultrasonic element drive/output signal line 146 as EM wave noise. Usually, these noises are minute, but may appear as periodic noise components in an ultrasonic image when superimposed.

In a connection line to the image sensor 16 and the ultrasound probe 20 in the electronic endoscope, a noise component is suppressed using a shielding material. Specifically, a noise component is suppressed using a reflection loss, an absorption loss, and a multiple reflection correction of the shielding material. The reflection loss is a loss caused by reflection of the shielding material. The absorption loss is a loss caused by an induced current flowing when EM waves are incident on the shielding material. In the multiple reflection correction, a noise component is suppressed by utilizing the fact that a part of EM waves that have entered the inside of the shielding material is reflected at the boundary and leaks to the outside while the reflection is repeated a plurality of times. In the multiple reflection correction, correction is performed in consideration of the thickness of the shielding material, a skin effect, and the wavelength of the EM wave.

When a noise control measure of the insertion portion 54 by such a shielding material is taken, the outer diameter of the insertion portion 54 becomes large, and thus the diameter of the insertion portion 54 cannot be sufficiently reduced. In addition, in a case where the drive signal or the output signal is made into a minute signal or a high-frequency signal in order to improve the device performance of the electronic endoscope 12, a noise component problem is likely to occur, which may adversely affect image quality improvement of an ultrasonic image. Therefore, it is difficult to suppress a noise component by the shielding material.

The periodically generated noise component is not caused by one factor, but is considered to be a complex phenomenon of various noise components. In order to improve the image quality of an ultrasonic image by suppressing the periodically generated noise component, it is necessary to detect a noise component that is periodically generated in an echo signal at a level equal to or higher than a preset threshold level and suppress the detected noise component. Here, a method of suppressing the noise component includes a method of suppressing an echo signal from including the noise component and a method of performing image processing on a two-dimensional B-mode image obtained from an echo signal including the noise component to eliminate a noise pixel.

Suppression of Noise Component

Figure 13:
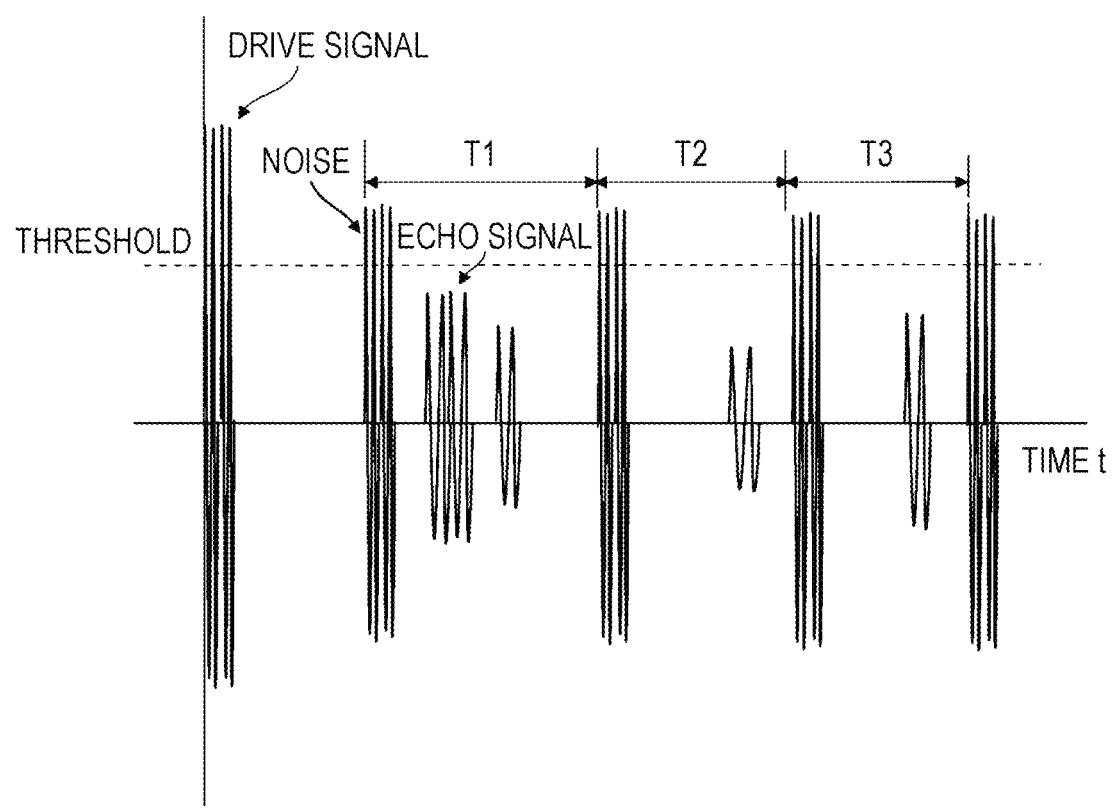
FIG. 13 is a diagram illustrating an example of an echo signal on which a periodically generated noise component is superimposed in the electronic endoscope system of an embodiment.

FIG. 13 is a diagram illustrating an example of an echo signal on which the periodically generated noise component is superimposed in the electronic endoscope system of an embodiment. As illustrated in FIG. 4, the noise component is a waveform corresponding to a high-brightness portion in a B-mode image and having an amplitude larger than that of an echo signal reflected by a living tissue by a drive signal of the ultrasound probe 20. Therefore, the noise detection unit 34 determines and detects a signal equal to or higher than a preset threshold level as a noise component.

As described above, the noise component is detected in a manner in which whether or not there is a spectral peak equal to or higher than a set threshold level is determined by performing frequency analysis using FFT for the digital echo signal.

Suppression of Amplification Gain of Noise Component

Figure 14:
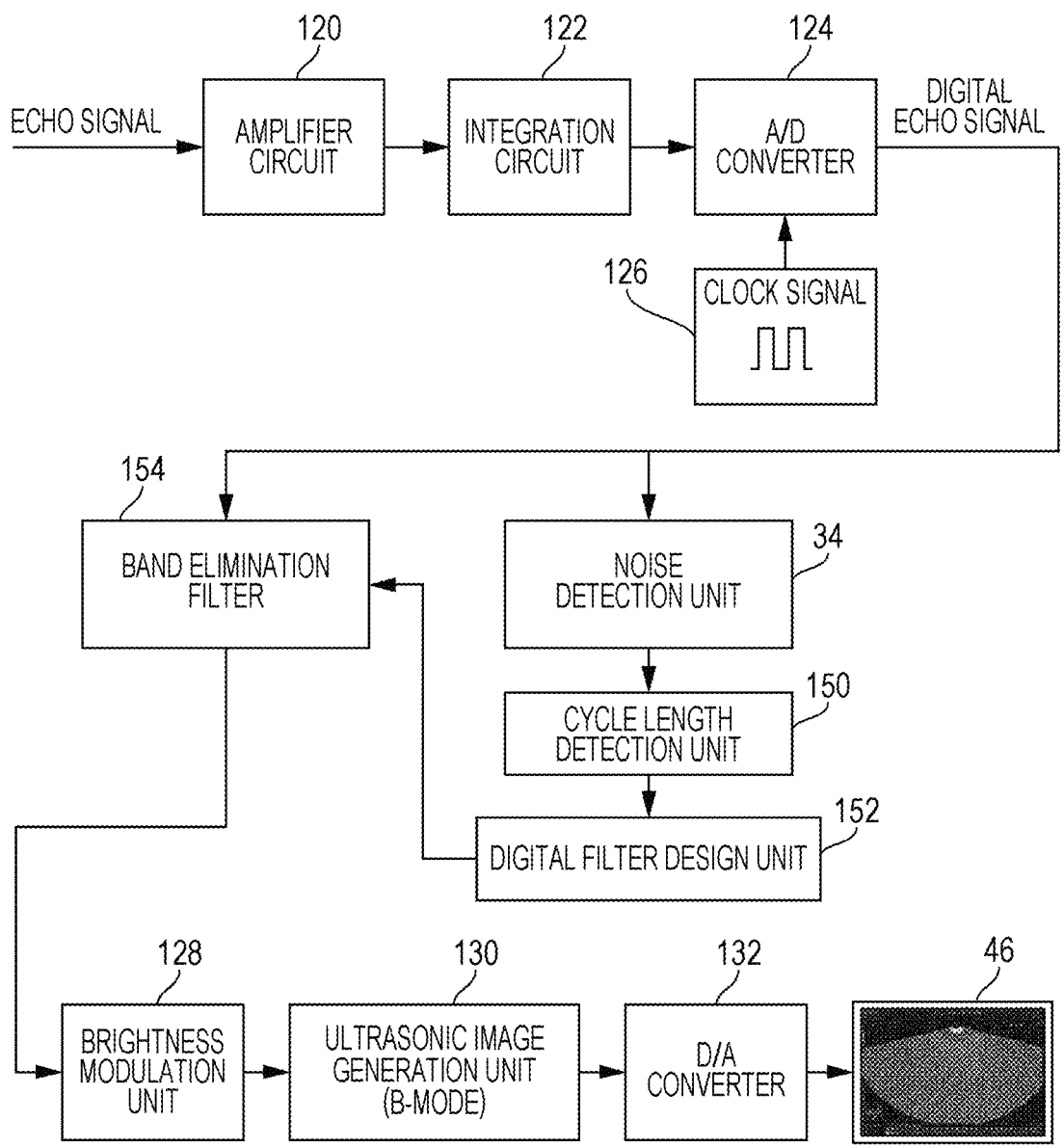
FIG. 14 is a diagram illustrating an example of a noise suppression unit by a band elimination filter used in the electronic endoscope system of an embodiment.

FIG. 14 is a diagram for describing an example of a method of changing an amplification gain of a noise pixel value in an ultrasonic image obtained by the electronic endoscope system of an embodiment. An echo signal becomes a digital echo signal by passing through the amplifier circuit 120, the integration circuit 122, and the A/D converter 124. The noise detection unit 34 sets a threshold of a noise level in advance and determines a signal equal to or higher than the threshold as a noise component. A cycle length detection unit 150 measures a cycle (T1, T2, T3, . . . ) of a digital echo signal detected as a noise component. At this time, the digital echo signal may be a part of random noise, and it is preferable to exclude a short cycle that is shorter than or equal to a certain cycle.

The cycle length detection unit 150 is provided in the noise detection unit 34 of the ultrasonic image processor 30 illustrated in FIG. 1. The cycle (T1, T2, T3, . . . ) can be obtained, for example, by specifying a plurality of generation time points of a noise component using a cycle calculated from a peak frequency of a power spectrum obtained by frequency analysis using FFT for a digital echo signal from the waveform of the digital echo signal displayed in the A-mode and calculating a time interval between the generation time points. As described above, the cycle length detection unit 150 calculates the cycle length and detects a noise component using the noise cycle and the cycle length, as a result of which the detection accuracy is high.

The measured cycle (T1, T2, T3, . . . ) varies within a certain range, and the cycle length detection unit 150 obtains the range of variation, the maximum value Tmax of the cycle, and the minimum value Tmin of the cycle. A digital filter design unit 152 uses the cycle length detected by the cycle length detection unit 150 as a bandwidth in the frequency domain, and designs a band elimination filter 154 that eliminates a frequency band with the minimum frequency 1/Tmax and the maximum frequency 1/Tmin (sets an elimination band). As the digital echo signal passes through the band elimination filter 154, even in a case where a noise component is periodically generated in the echo signal, the amplitude of the noise component can be suppressed, as a result of which a periodic noise component in a B-mode image can be suppressed.

Gain change processing preferably includes a band elimination filter that obtains a frequency band corresponding to a noise cycle based on the noise cycle and the cycle length and eliminates a noise component from an echo signal by using the frequency band, and is preferably performed in time series. Note that, in characteristics of the band elimination filter, an elimination bandwidth is set in such a way that a frequency band corresponding to a varying cycle (T1, T2, T3, . . . ) becomes the elimination band.

Figure 15:
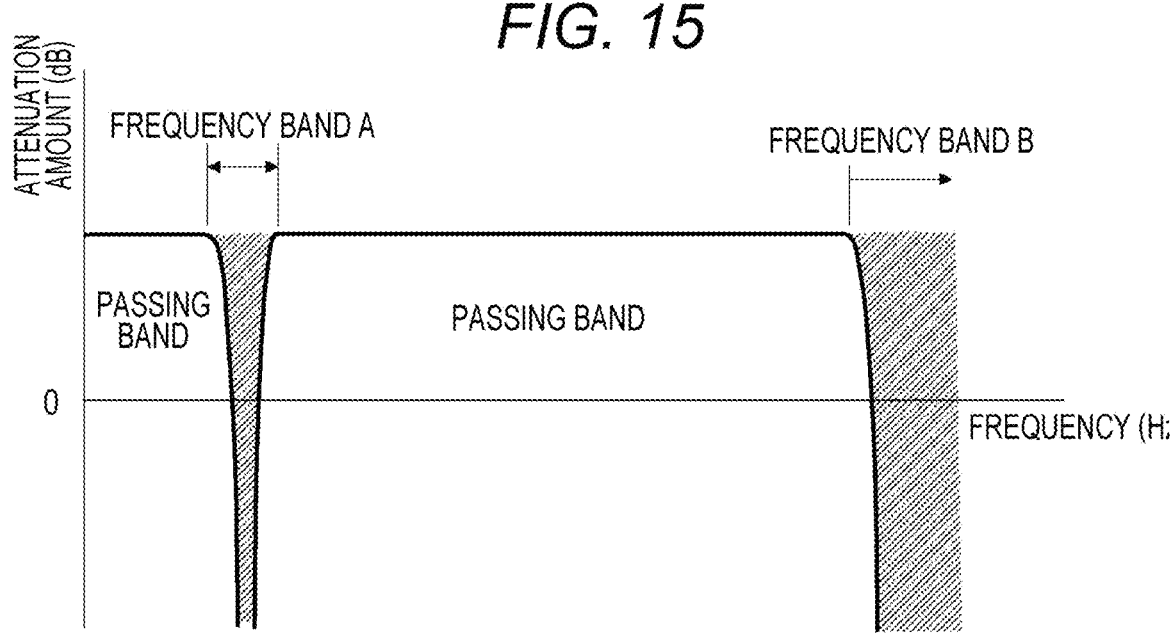
FIG. 15 is a diagram illustrating an example of frequency characteristics of all filters that filter an echo signal in the electronic endoscope system of an embodiment.

FIG. 15 is a diagram illustrating frequency characteristics of all filters that filter an echo signal. An echo signal is filtered by the integration circuit 122 and the band elimination filter 154. In the integration circuit 122, a frequency band B of a random harmonic noise component is suppressed, and a periodically generated noise component is suppressed in a low frequency band A.

Figure 16:
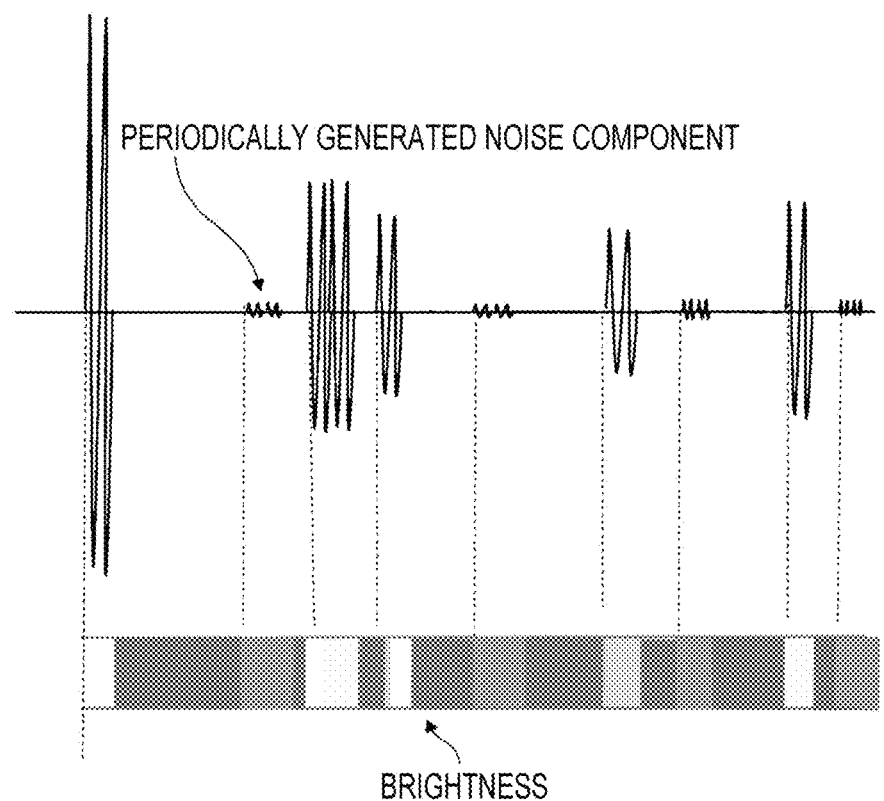
FIG. 16 is a diagram illustrating an example of a digital echo signal after an echo signal including periodically generated noise obtained by the electronic endoscope system according to an embodiment passes through a band elimination filter and a brightness.

FIG. 16 is a diagram illustrating an example of a digital echo signal after an echo signal including periodically generated noise obtained by the electronic endoscope system according to an embodiment passes through the band elimination filter. Harmonic noise is suppressed by the integration circuit 122, and a digital echo signal after passing through the band elimination filter 154 is also suppressed. As a result, a periodically generated noise component in a brightness signal obtained by the brightness modulation unit 128 is suppressed.

Note that amplification gain adjustment may be configured such that, instead of the band elimination filter 154, a brightness modulation unit 128 that converts a digital echo signal into a brightness signal decreases an amplification gain value of a signal corresponding to a noise component based on information specifying a time point when the noise component is generated, thereby decreasing the brightness value. As a result, even in a case where a noise component is periodically generated in an echo signal, the amplitude of the noise component can be suppressed by adjusting the amplification gain, and a periodic noise component in a B-mode image can be suppressed.

Interpolation Processing of Noise Pixel Value

In the electronic endoscope system of an embodiment, it is also possible to perform interpolation processing by eliminating a noise pixel from an ultrasonic image obtained as a B-mode image in the electronic endoscope system of an embodiment.

Figure 17:
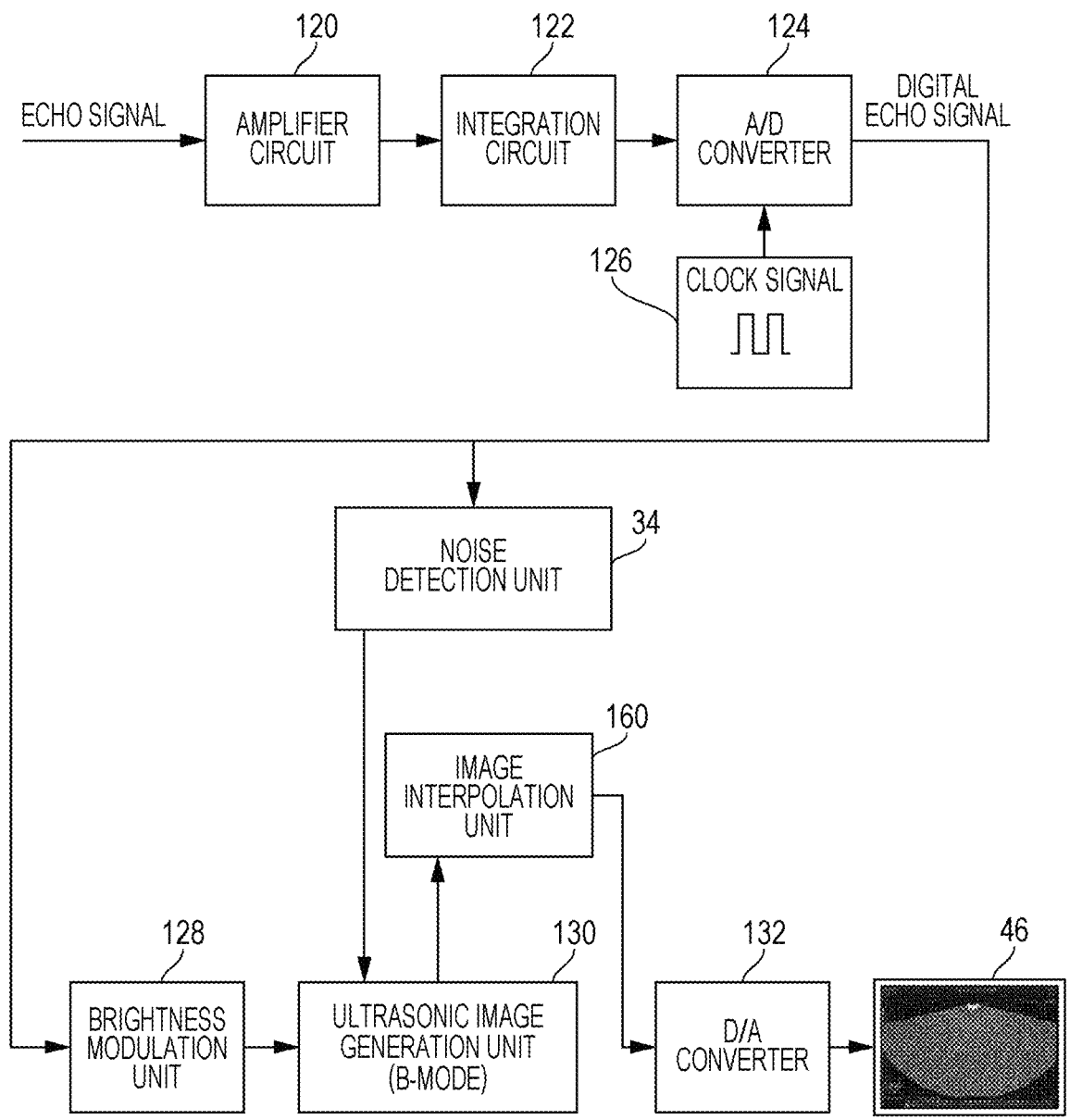
FIG. 17 is a diagram for describing an example of the noise suppression unit that performs interpolation processing by eliminating a noise pixel from an ultrasonic image obtained as a B-mode image in the electronic endoscope system of an embodiment.

FIG. 17 is a diagram for describing an example of the noise suppression unit that performs interpolation processing by eliminating a noise pixel from an ultrasonic image obtained as a B-mode image in the electronic endoscope system of an embodiment. In an ultrasonic image (B-mode image) generated by the ultrasonic image generation unit 130, a noise pixel corresponding to a periodically generated noise component detected by the noise detection unit 34 is replaced with an interpolation pixel value generated based on pixel values of peripheral pixels by an image interpolation unit 160. The image interpolation unit 160 is provided in the noise suppression unit 36 of the ultrasonic image processor 30 illustrated in FIG. 1.

For example, the image interpolation unit 160 performs pixel interpolation by using four peripheral pixels adjacent to four sides of a noise pixel. The pixel value of the noise pixel is pixel-interpolated using the pixel values of the four adjacent peripheral pixels. For example, an average value of the pixel values of the four peripheral pixels is set as the pixel value of the noise pixel. This interpolation method is a method called bilinear interpolation, but the interpolation method may be another method. For example, bicubic interpolation is used. In a case where noise pixels are adjacent to each other, the image interpolation unit 160 searches for a pixel adjacent to the noise pixels until a non-noise pixel adjacent to the noise pixels is found, and performs pixel interpolation by using pixel values of a plurality of non-noise pixels surrounding the region of the noise pixels.

As described above, since the noise suppression unit 36 performs correction processing of replacing a pixel value of a detected noise component at a noise pixel position in an ultrasonic image with an interpolation pixel value generated based on pixel values of peripheral pixels positioned around the noise pixel position, it is possible to suppress a noise component in a B-mode image even in a case where the noise component is periodically generated in an echo signal.

Elimination of Power Supply Noise

The switching power supply is often used as a power supply for supplying power to be supplied to each device of the electronic endoscope system 10. In this case, as described above, a noise component is generated due to the influence of the switching operation of the switching power supply. In order to suppress this noise component, it is preferable to change the switching frequency in the DC/DC converter and the switching frequency in the AC/DC converter. Furthermore, in order to eliminate the noise component, it is preferable to use a storage battery that does not perform the switching operation.

Figure 18:
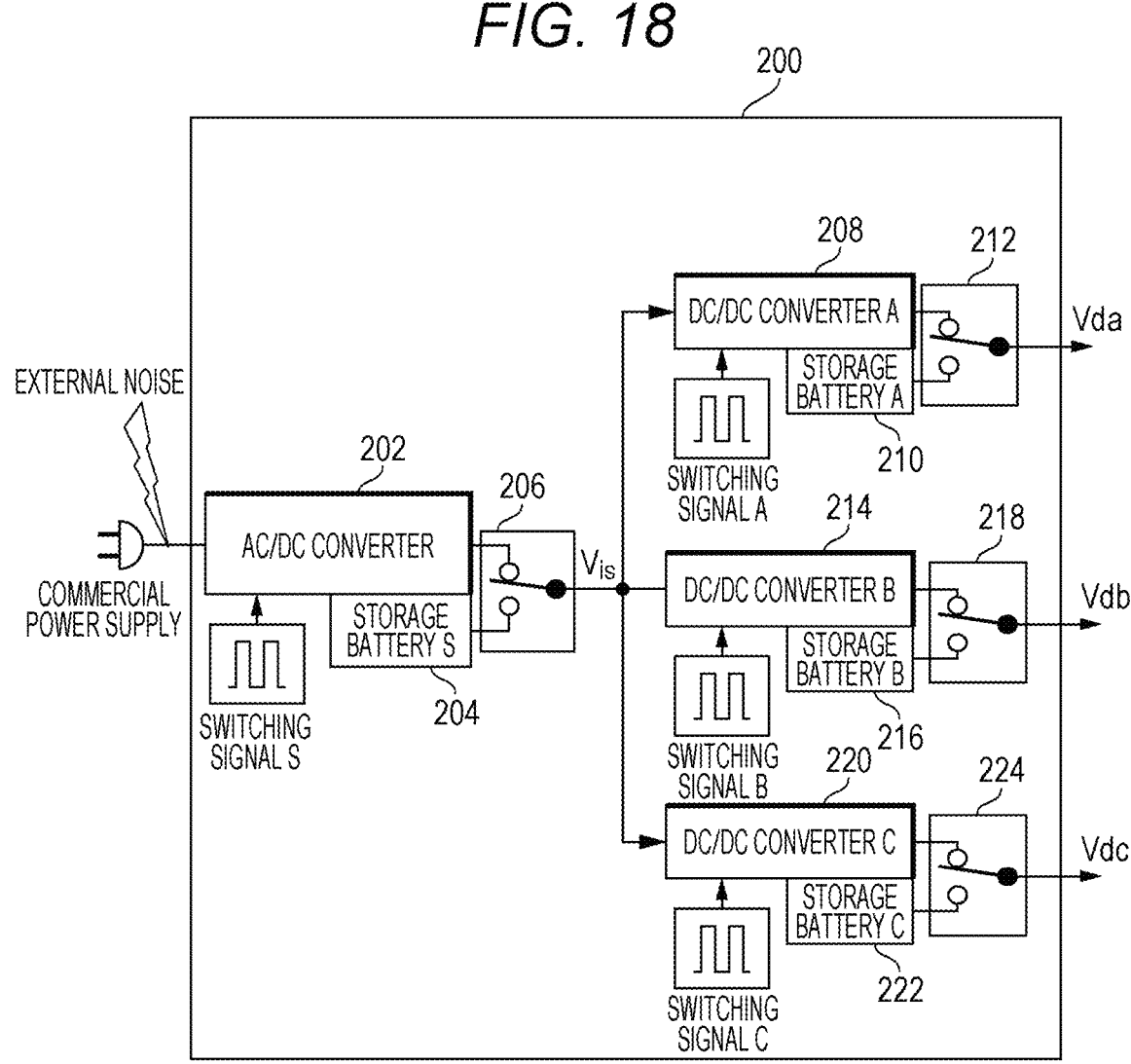
FIG. 18 is a diagram illustrating an example in which a switching power supply and a storage battery are provided together and switching means is provided in the electronic endoscope system of an embodiment.

FIG. 18 is a diagram illustrating an example in which the switching power supply and the storage battery are provided together and switching means is provided in the electronic endoscope system of an embodiment. An AC/DC converter 202 outputs a DC voltage Vis by switching a commercial AC power supply as an input voltage according to a switching signal S. A storage battery S204 is provided together in the AC/DC converter 202, and a switching switch S206 performs switching between the AC/DC converter 202 as the switching power supply and the storage battery S204. As a result, the DC voltage Vis becomes a voltage that does not include a noise component due to the switching operation. Once switching to the storage battery S204 is made, the AC/DC converter 202 stops its operation, as a result of which external noise entering the commercial power supply can be cut off The DC voltage Vis output from the AC/DC converter 202 is an input voltage of a DC/DC converter A206, a DC/DC converter B214, and a DC/DC converter C220. A storage battery A210 is provided together in a DC/DC converter A208, and a switching switch A212 performs switching between the DC/DC converter A208 as the switching power supply and the storage battery A210. Similarly, a storage battery B216 and a storage battery C222 are provided together in the DC/DC converter C220, and a switching switch B218 and a switching switch C224 perform switching for the storage battery B216 and the storage battery C222, respectively.

The storage battery S104, the DC/DC converter A208, the DC/DC converter B214, and the DC/DC converter C220 are effective not only as noise control measures but also as emergency power supplies when an AC outlet is disconnected for some reason or a power failure occurs. In addition, it is preferable that each converter also charges the storage battery provided together. As a result, each storage battery is always charged and can be switched and used at any time.

Figure 19A:
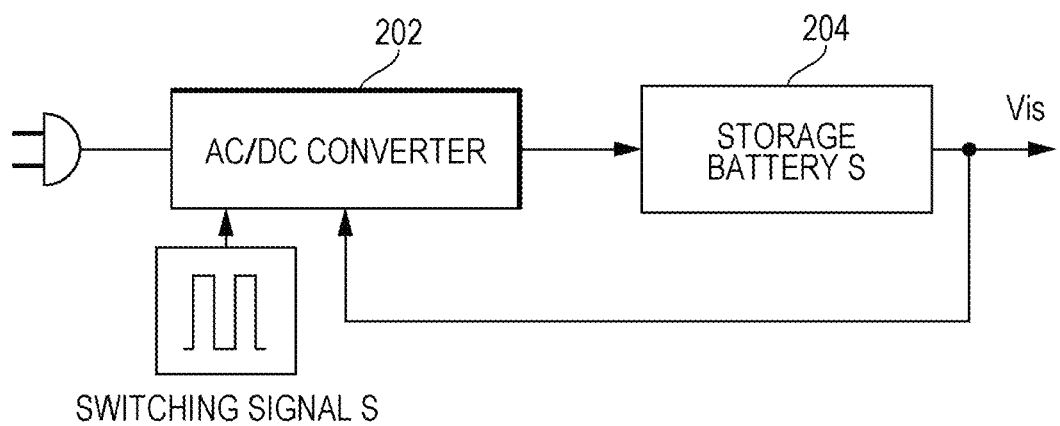
FIG. 19A is a diagram illustrating an example in which a converter is used as a power supply dedicated to charging of the storage battery provided together in the electronic endoscope system of an embodiment.
Figure 19B:
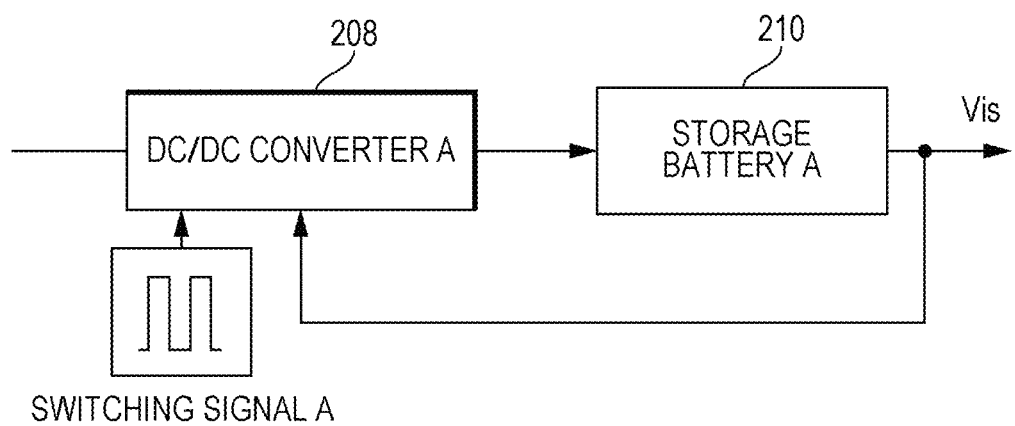
FIG. 19B is a diagram illustrating an example in which a converter is used as the power supply dedicated to charging of the storage battery provided together in the electronic endoscope system of an embodiment.

FIGS. 19A and 19B are diagrams illustrating examples in which a converter is used as a power supply dedicated to charging of the storage battery provided together in the electronic endoscope system of an embodiment. In a case where a storage battery is provided together in each converter, the storage battery which does not generate noise due to the switching operation may be mainly used, and the converter may be used as a dedicated power supply for the storage battery. The capacity of the storage battery in this case can be smaller than that of the method using switching as illustrated in FIG. 18. In a case where the AC/DC converter 202 is used as a power supply dedicated to charging the storage battery S204 provided together, an output voltage Vis of the storage battery S204 is fed back to the AC/DC converter 202, and the storage battery S204 is controlled to have a constant output voltage Vis. This control may be control by turning on/off of the switching signal S.

FIG. 19B illustrates an example in which the DC/DC converter A208 is a power supply dedicated to charging the storage battery A210 provided together. An output voltage Vda of the storage battery A210 is fed back to the DC/DC converter A208, and is controlled such that the storage battery A210 has a constant output voltage Vda. The DC/DC converter B214 and the DC/DC converter C220 can be configured in the same manner. The output voltages Vda, Vdb, and Vdc are different voltage values and correspond to supply voltages of the component devices.

For this purpose, a plurality of DC/DC converters are used. In a storage battery, single cells having an output voltage of about 1 V to 3 V are connected in series in order to output an arbitrary voltage value. The arbitrary voltage value is obtained by the number of single cells connected in series. Therefore, in a case where the output voltage of the AC/DC converter 202 can be individually charged in a single cell of a storage battery, the DC/DC converter A208, the DC/DC converter B214, and the DC/DC converter C220 can be made unnecessary.

Furthermore, in order to suppress a noise component, the noise suppression unit 36 preferably changes at least one of the operation frequencies of the plurality of component devices included in the captured image processor 22 and the ultrasonic image processor 30 so as to be separated from a generation cycle of a noise component periodically generated in an echo signal.

In this case, as described above, it is preferable that the DC/DC converters as the switching power supplies for driving the electronic endoscope 12, the captured image processor 22, and the ultrasonic image processor 30 are provided as the component devices, and it is preferable to change the switching frequencies for the DC/DC converter A208, the DC/DC converter B214, and the DC/DC converter C220 as the operation frequencies of the component devices to be changed so as to be separated from a generation cycle of a noise component periodically generated in an echo signal. As a result, a noise component periodically generated in an echo signal can be suppressed in some cases.

It is preferable to change the switching frequency for the AC/DC converter 202 as the operation frequency of the component device to be changed so as to be separated from a generation cycle of a noise component periodically generated in an echo signal. As a result, a noise component periodically generated in an echo signal can be suppressed in some cases.

Furthermore, at least one of an ultrasonic frequency of the ultrasound probe 20 or an image sensor operation frequency of the image sensor 16 may be set as the operation frequency of the component device to be changed. As a result, a noise component periodically generated in an echo signal can be suppressed in some cases.

Furthermore, a sampling frequency of an echo signal in the A/D converter 124 may be set as the operation frequency of the component device to be changed. As a result, a noise component periodically generated in an echo signal can be suppressed in some cases.

As described above, the ultrasonic image processor 30 detects a noise component included in an echo signal and periodically generated at a level equal to or higher than a preset threshold level, and performs processing of suppressing the detected noise component, so that it is possible to generate a high-quality ultrasonic image.

More specifically, in the electronic endoscope system 10, various noises are superimposed on an echo signal output from the ultrasound probe 20, and many of the noises are random noises including harmonic components. Therefore, image quality improvement is achieved by eliminating the harmonic components. However, it is considered that a periodically generated noise component is generated in such a way that many signals and harmonics thereof are in synchronization with each other, and a cycle at which the harmonics are synchronized is in a low frequency region and has a large amplitude. Therefore, the ultrasonic image processor 30 includes the noise detection unit 34, an echo signal periodically generated at a level equal to or higher than a preset threshold level is determined as noise, the noise component is suppressed by the suppression unit 36.

Therefore, in the electronic endoscope system 10, a threshold level is provided to detect a noise component by using the fact that periodically generated noise is a noise component having a large amplitude. Meanwhile, since the suppression unit 36 suppresses a noise component in such a way that the detected noise component becomes small, it is possible to obtain a high-quality ultrasonic image.

Figure 20:
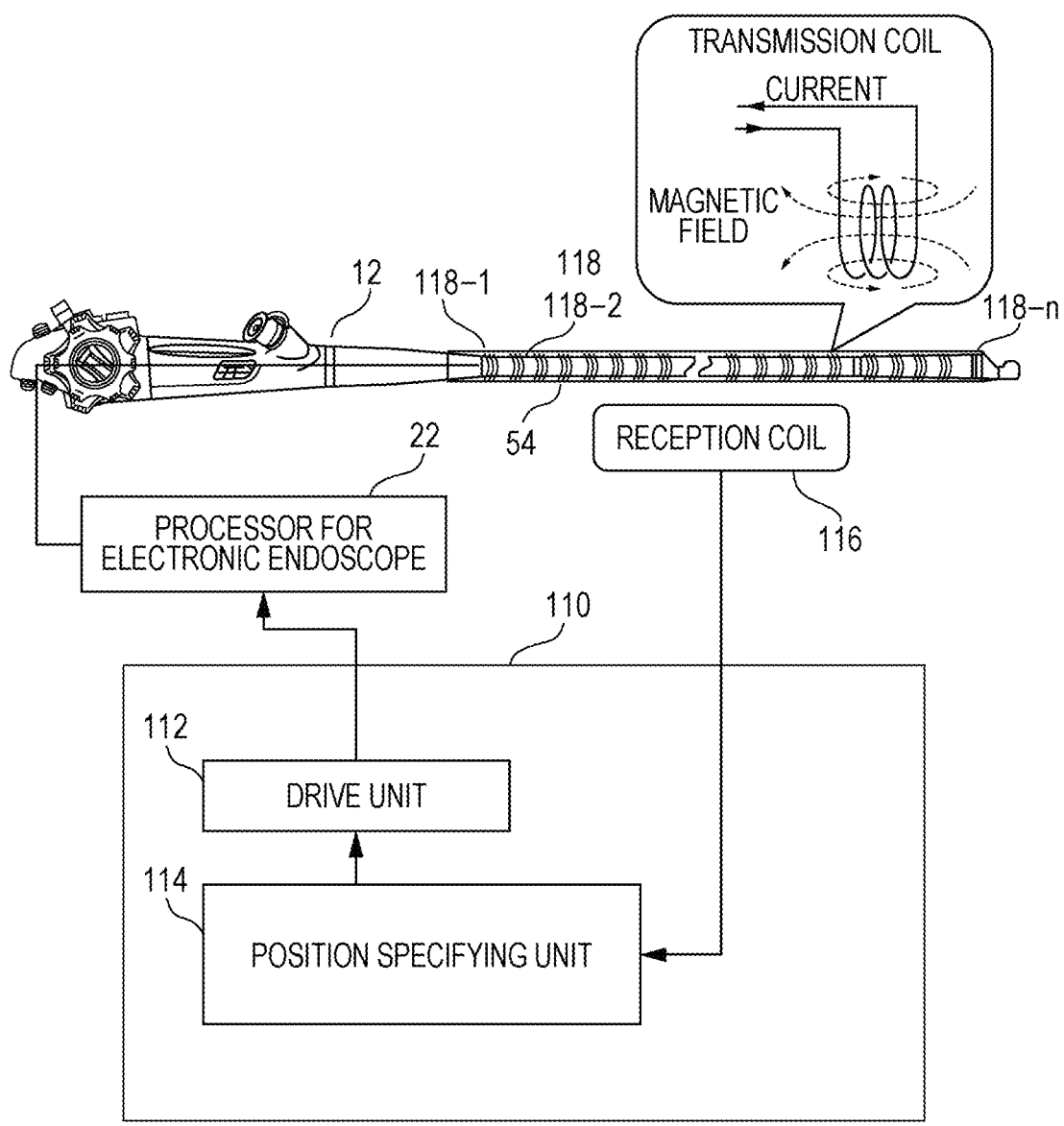
FIG. 20 is a diagram schematically illustrating an example of an electronic endoscope position measurement device used in the electronic endoscope system of an embodiment.

Note that, when using the electronic endoscope system 10, the electronic endoscope position measurement device 110 capable of specifying the position of the electronic endoscope 12 inserted into the body cavity in the body cavity by using magnetism is used in some cases. FIG. 20 illustrates an example of the electronic endoscope position measurement device 110.

FIG. 20 is a diagram schematically illustrating an example of the electronic endoscope position measurement device used in the electronic endoscope system 10 of an embodiment. A plurality of transmission coils 118 used in the electronic endoscope position measurement device 110 are wound around the insertion portion 54 of the electronic endoscope 12 at predetermined intervals, and generates a magnetic field by a current. The plurality of transmission coils 118-1, 118-2, . . . , and 118-*n* generate a magnetic field at each position when the electronic endoscope 12 is inserted into the body cavity, and a reception coil 116 receives the magnetic field to measure the position of the endoscope. Note that FIG. 20 illustrates a case where the transmission coil 118 is provided in the insertion portion 54 and the reception coil 116 is provided at the outside, but the transmission coil 118 may be provided at the outside and the reception coil 116 may be provided in the endoscope.

The reception coil 116 includes a plurality of coil blocks and is arranged, for example, beside a bed. Each coil block of the reception coil 116 is wound in such a way that coil surfaces thereof are orthogonal to each other in three directions. The coil detects a signal proportional to the strength of a magnetic field of an axial component orthogonal to the coil surface. The coil block receives the generated magnetic field, converts the magnetic field into a voltage signal, and outputs the voltage signal as a detection result. The operation states of the transmission coil 118 and the reception coil 116 are controlled by a drive unit 112.

Each of the transmission coils 118-1, 118-2, . . . , and 118-*n* is supplied with high-frequency sine waves from the drive unit 112 via the captured image processor 22. As the sine waves are applied, each of the transmission coils 118-1, 118-2, . . . , and 118-*n* radiates electromagnetic waves accompanied by a magnetic field to the surroundings. Note that the drive unit 112 can also individually designate a timing at which each of the transmission coils 118-1, 118-2, . . . , and 118-*n* generates a magnetic field.

The reception coil 116 receives the magnetic field generated by the transmission coil 118, generates a current by the received magnetic field, and converts the current into a voltage signal. The signal is transmitted from the reception coil 116 to the drive unit 112. The drive unit 112 provides a signal from the reception coil 116 to a position specifying unit 114, performs predetermined signal processing such as amplification processing, and then converts the signal into digital data by A/D conversion.

In specifying the position, a frequency is extracted from the digital data by the fast Fourier transform, and separated and extracted as magnetic field detection information of the frequency component corresponding to the sine waves of each of the transmission coils 118-1, 118-2, . . . , and 118-*n*. Spatial position coordinates of the respective transmission coils 118-1, 118-2, . . . , and 118-*n* provided in the ultrasound probe 20 are calculated from digital data of the separated magnetic field detection information. Further, the position specifying unit 114 connects the position coordinates of the transmission coils 118-1, 118-2, . . . , and 118-*n* to generate a linear insertion shape image as an electronic endoscope position image.

The length from the position of the coil positioned at an inlet portion of the insertion portion to the position of the coil positioned at the distal end of the insertion portion can also be calculated as an insertion length.

In a case of using such an electronic endoscope position measurement device 110, when a noise component is periodically generated in an echo signal, it is preferable to change at least one operation frequency of the electronic endoscope position measurement device 110 as one component device so as to be separated from a generation cycle of the noise component periodically generated in the echo signal. The drive signal of the transmission coil 118 may cause a noise component periodically generated in an echo signal. Therefore, it is preferable to control the drive unit 112 so as to change the frequency of the drive signal as the operation frequency. Alternatively, it is preferable that the noise suppression unit 36 controls the drive unit 112 to stop the transmission of the drive signal in order to stop the generation of the magnetism of the transmission coil 118 generated when a noise component is detected. As a result, a noise component periodically generated in an echo signal can be suppressed in some cases.

Although a noise component is detected using a preset threshold or using frequency analysis in the embodiment described above, a noise component may also be detected using a prediction model subjected to machine learning, that is, using artificial intelligence (AI).

In the detection using AI, the noise detection unit 34 extracts a feature amount by machine learning using, as training data, a training ultrasonic image without an echo signal in which a noise component is periodically generated and a training ultrasonic image in which a noise component is periodically generated. As a result, the presence or absence of a periodic noise component can be learned in advance. The presence or absence of a periodic noise component of an input ultrasonic image is determined based on the learning result.

Figure 21:
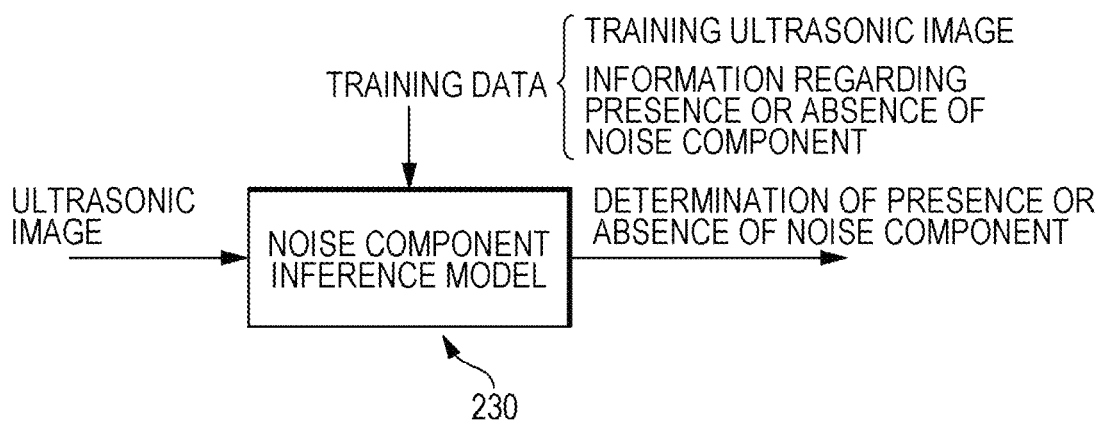
FIG. 21 is a diagram for describing an example of a process of training artificial intelligence (AI) and determining the presence or absence of a periodically generated noise component in the electronic endoscope system of an embodiment.

FIG. 21 is a diagram for describing an example of a process of training artificial intelligence (AI) and determining the presence or absence of a periodically generated noise component in the electronic endoscope system of an embodiment. A noise component inference model 230 is created by extracting a feature amount by machine learning from a training ultrasonic image to which information on the presence or absence of a noise component is given. It is possible to determine the presence or absence of a noise component from a feature amount extracted inside by the noise component inference model 230 by inputting an ultrasonic image to the noise component inference model 230. Examples of the feature amount include the amplitude of the noise component, the periodicity of the noise component, and the spread of the noise component.

Figure 22:
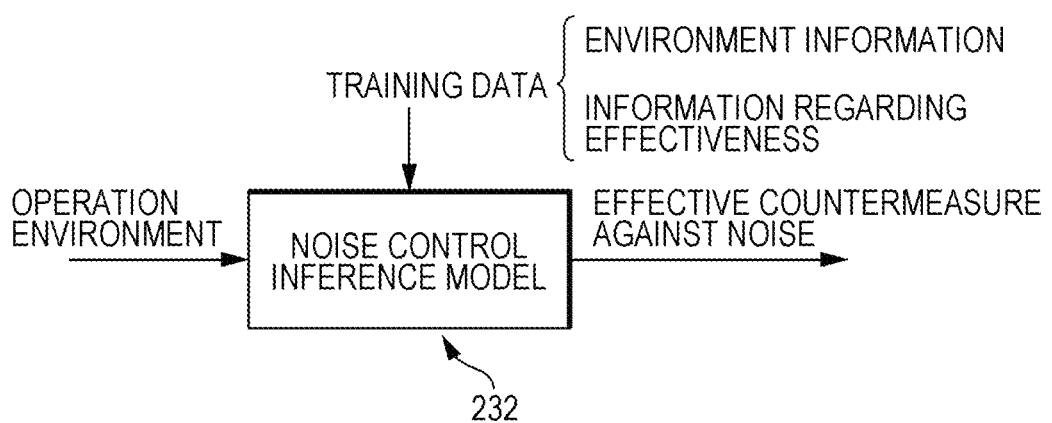
FIG. 22 is a diagram for describing an example of inferring an effective countermeasure against noise by the AI in the electronic endoscope system of an embodiment.

FIG. 22 is a diagram for describing an example of inferring an effective countermeasure against noise by the AI in the electronic endoscope system of an embodiment. Noise suppression by the AI is performed using a noise control inference model 232. The noise control inference model 232 is A-model that has learned, by machine learning, a relationship between an operation environment information of the electronic endoscope, the captured image processor, or the ultrasonic image processor and a feature amount of an ultrasonic image and information regarding whether a countermeasure for suppressing a noise component is effective or ineffective according to the feature amount and the operation environment information, in the noise suppression unit 36.

When a noise component is detected in a newly generated ultrasonic image, the noise detection unit 34 extracts a feature amount of the ultrasonic image, and inputs operation environment information when the noise component is detected and the extracted feature amount to the created noise control inference model 232, thereby setting a change content of the environment operation information effective for noise suppression. The suppression unit 36 changes the operation environment of the electronic endoscope 12, the captured image processor 22, the ultrasonic image processor 30, or the electronic endoscope position measurement device 110 based on the set environment operation information. Periodic noise is suppressed by changing the operation environment.

The noise component inference model 230 of the noise detection unit 34 and the noise control inference model 232 of the noise suppression unit 36 are created using, for example, a neural network. As the neural network, for example, a convolutional neural network widely applied in image recognition is suitably used.

The operation environment information preferably includes operation frequencies of a plurality of component devices included in the captured image processor 22 and the ultrasonic image processor 30. The operation frequencies preferably include an ultrasonic frequency of the ultrasound probe 20 and an operation frequency of the image sensor 16, a sampling frequency of an echo signal in the A/D converter 124, switching frequencies in the DC/DC converters 208, 214, and 220, a switching frequency in the AC/DC converter 202, and an operation frequency of the transmission coil 118 of the electronic endoscope position measurement device 110. Since such operation frequencies are changed by the AI, noise suppression can be effectively performed.

Figure 23:
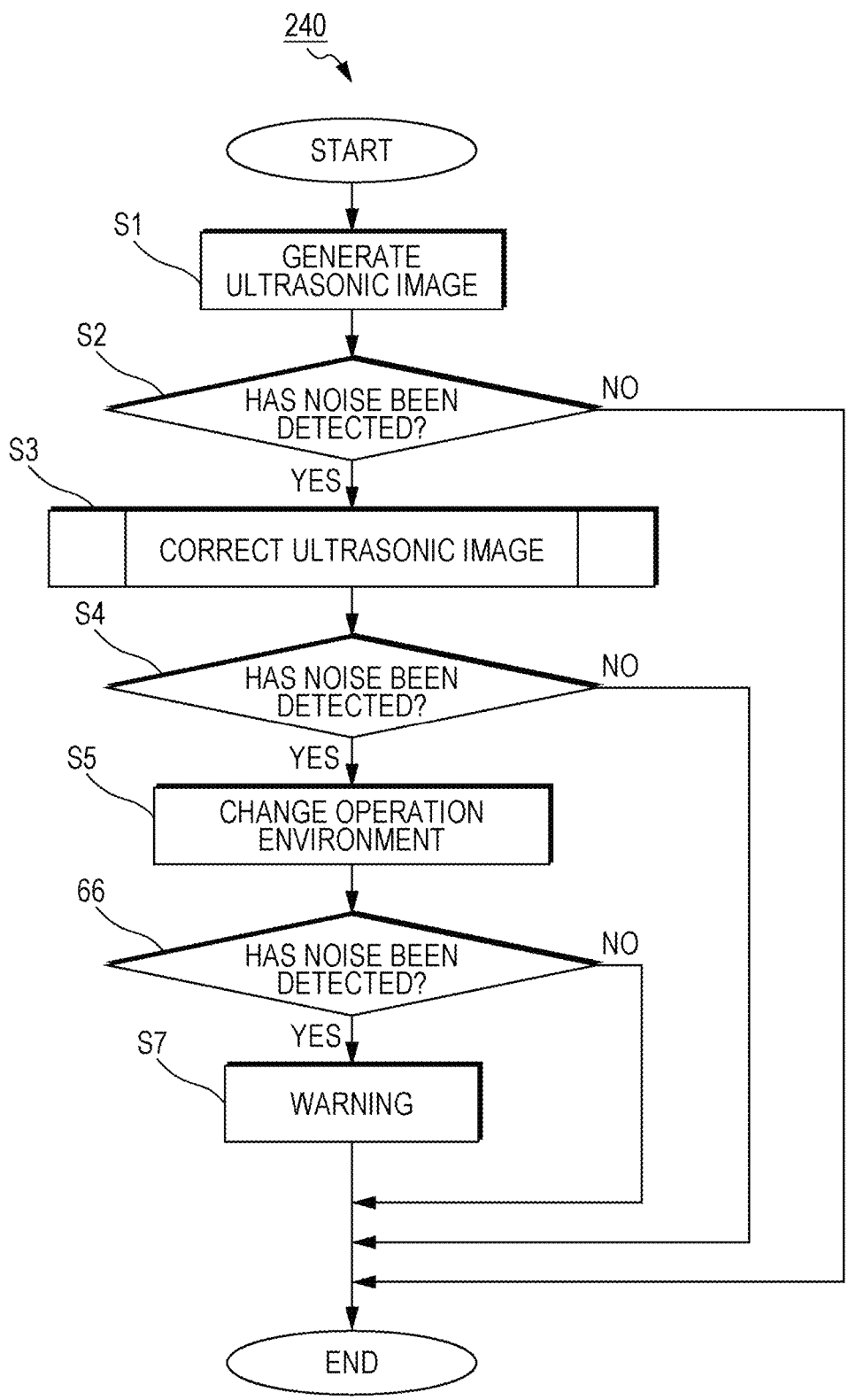
FIG. 23 is a diagram illustrating an example of an operation flow of noise correction performed in the electronic endoscope system of an embodiment.

FIG. 23 is a diagram illustrating an operation flow of noise correction. First, in Step S1, an ultrasonic image is generated. The ultrasonic image is generated by the ultrasonic image generation unit 130 after an echo signal from the ultrasound probe 20 is converted into grayscale pixels by the brightness modulation unit 128. In Step S2, periodic noise is detected. In detecting noise, a signal equal to or greater than a predetermined threshold value is detected as noise. In a case where no noise is detected, the processing ends.

In a case where noise has been detected, ultrasonic image correction is performed. The ultrasonic image correction is performed by the band elimination filter 154 or the image interpolation unit 160. In Step S4, noise detection is performed again to confirm whether or not noise has been corrected by ultrasonic image correction. In a case where no noise is detected, the processing ends. In a case where noise has been detected, in Step S5, the operation environment including the operation frequencies of the plurality of component devices included in the electronic endoscope 12, the captured image processor 22, the ultrasonic image processor 30, and the electronic endoscope position measurement device 110 is changed. The operation environment to be changed includes the operation frequencies of the plurality of component devices included in the electronic endoscope 12, the captured image processor 22, the ultrasonic image processor 30, and the electronic endoscope position measurement device 110.

The operation frequencies include an ultrasonic frequency of the ultrasound probe 20 and an operation frequency of the image sensor 16, a sampling frequency of an echo signal in the A/D converter 124, switching frequencies in the DC/DC converters 208, 214, and 220, a switching frequency in the AC/DC converter 202, and an operation frequency of the transmission coil 118 of the electronic endoscope position measurement device 110. The operation of the image sensor 16 or the transmission coil 118 may be stopped. Further, the DC/DC converters 208, 214, and 220 and the AC/DC converter 202 may be replaced with storage batteries.

In Step S6, noise detection is performed again in order to confirm the effect of the changed operation environment. In a case where no noise is detected, the processing ends. In a case where noise has been detected, a warning is given in Step S7, and the processing ends. The warning is displayed on the ultrasonic image display unit 46. In this case, an operator is notified of the presence of noise, thereby preventing diagnosis using the ultrasonic image from being affected.

Figure 24:
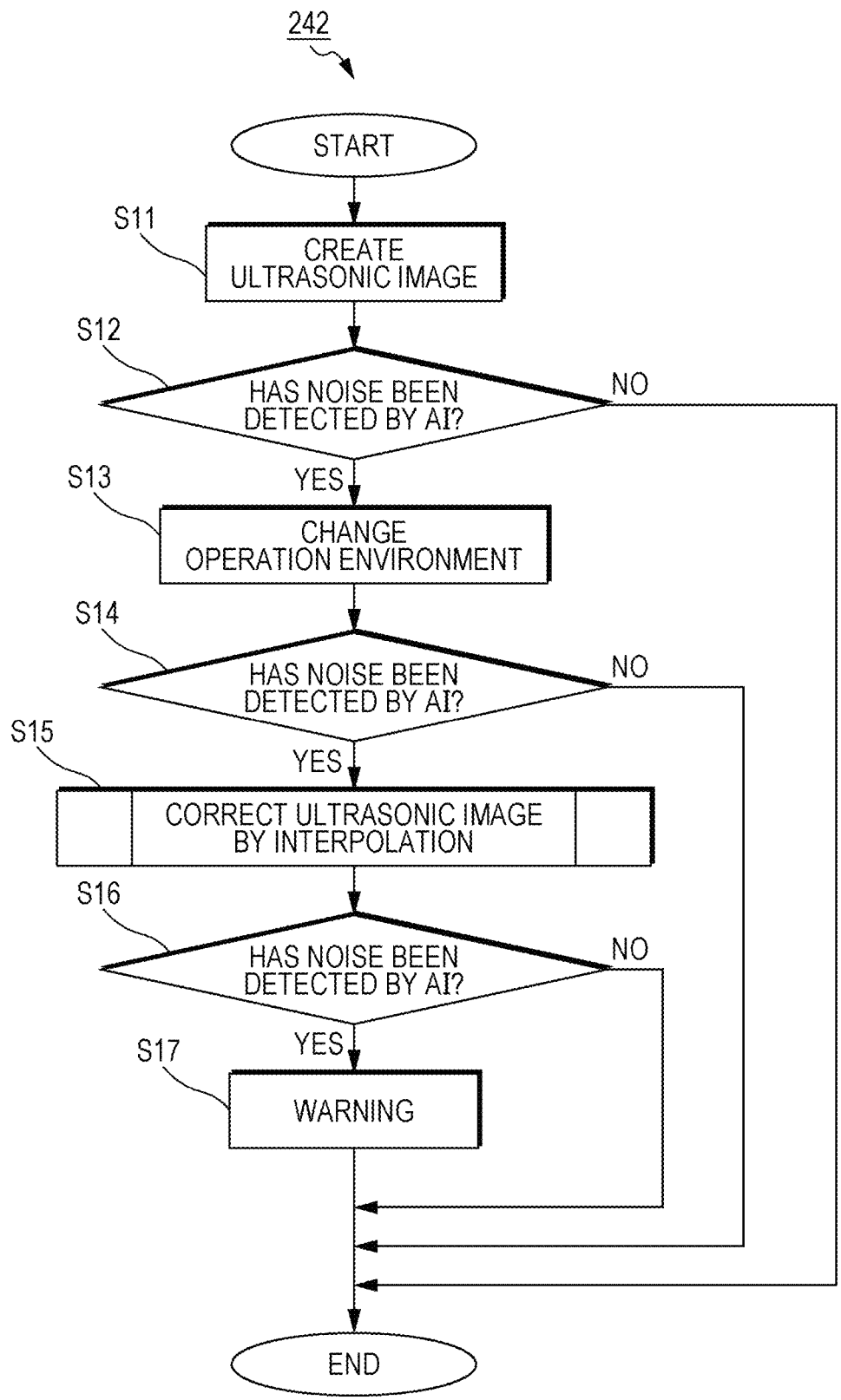
FIG. 24 is a diagram illustrating an operation flow of noise correction by the artificial intelligence (AI) performed in the electronic endoscope system of an embodiment.

FIG. 24 is a diagram illustrating an operation flow of noise correction by the AI. First, in Step S11, an ultrasonic image is generated. In Step S12, periodic noise is detected by the noise component inference model 230 in the noise detection unit 34. Noise is detected by the machine-learned noise component inference model 230. In a case where no noise is detected, the processing ends.

In Step S13, the operation environment including the operation frequencies of the plurality of component devices included in the electronic endoscope 12, the captured image processor 22, the ultrasonic image processor 30, and the electronic endoscope position measurement device 110 is changed. In the change of the operation environment, a feature amount of the ultrasonic image is extracted, the created noise control inference model 232 is applied to collate the feature amount, and a change content of the environment operation information effective for suppressing noise is set based on the collation result. The noise suppression unit 36 changes the operation environment of the electronic endoscope 12, the captured image processor 22, the ultrasonic image processor 30, or the electronic endoscope position measurement device 110 based on the set environment operation information.

The operation environment information includes the operation frequencies of the plurality of component devices included in the electronic endoscope 12, the captured image processor 22, the ultrasonic image processor 30, or the electronic endoscope position measurement device 110.

The operation frequencies include an ultrasonic frequency of the ultrasound probe 20 and an operation frequency of the image sensor 16, a sampling frequency of an echo signal in the A/D converter 124, switching frequencies in the DC/DC converters 208, 214, and 220, a switching frequency in the AC/DC converter 202, and an operation frequency of the transmission coil 118 of the electronic endoscope position measurement device 110. The operation of the image sensor 16 or the transmission coil 118 may be stopped. Further, the DC/DC converters 208, 214, and 220 and the AC/DC converter 202 may be replaced with storage batteries.

In Step S14, noise detection is performed again by the AI in order to confirm the effect of the changed operation environment. In a case where no noise is detected, the processing ends. In a case where noise has been detected, the ultrasonic image is corrected by interpolation in Step S15. In Step S16, noise detection is performed by the AI in order to confirm the correction effect for the ultrasonic image. In a case where no noise is detected, the processing ends. In a case where noise has been detected, a warning is given in Step S17, and the processing ends. The warning is displayed on the ultrasonic image display unit 46. In this case, an operator is notified of the presence of noise, thereby preventing diagnosis using the ultrasonic image from being affected.

The endoscope diagnosis data management system of the present invention is described above in detail, but the endoscope diagnosis data management system of the present invention is not limited to the above-described embodiment, and may of course be modified or altered in various ways in a range not deviating from the scope and spirit of the present invention.

The invention claimed is:

1. An electronic endoscope system that acquires an ultrasonic image, the electronic endoscope system comprising:
   an electronic endoscope including, at a distal end portion, an image sensor that captures an image of a living tissue, and an ultrasound probe that applies ultrasonic waves to the living tissue to obtain an echo signal;
   a captured image processor including an image processor that processes an imaging signal output from the image sensor and generates a captured image; and
   an ultrasonic image processor including an ultrasonic image processor that processes the echo signal output from the ultrasound probe and generates an ultrasonic image, a noise detector configured to determine either of the presence and absence of a noise component included in the echo signal, and a noise suppressor that performs processing of suppressing the detected noise component, wherein:
   upon the noise detector determining the presence of the noise component periodically generated at a level equal to or higher than a preset threshold level, the noise suppressor performs the processing of suppressing the detected noise component,
   upon the noise detector determining the absence of the noise component periodically generated at the level equal to or higher than the preset threshold level, the noise suppressor refrains from performing the processing of suppressing the detected noise component, and
   a generation frequency of the noise component periodically generated at the level equal to or higher than the preset threshold level corresponds to an interval of points separated from each other in the ultrasonic image, brightness of the points in the ultrasonic image corresponding to the echo signals acquired at different timing.

2. The electronic endoscope system according to claim 1, wherein the noise detector includes a cycle length detector that calculates a noise cycle in which the noise component is periodically generated and calculates a cycle length from a minimum value and a maximum value of the noise cycle, and the noise detector determines the presence or absence of the noise component periodically generated at the level equal to or higher than the preset threshold level by using the noise cycle and the cycle length.

3. The electronic endoscope system according to claim 1, wherein the noise suppressor performs gain change processing of changing an amplification gain value between a pixel value of the detected noise component at a noise pixel position in the ultrasonic image and a pixel other than a noise pixel at the noise pixel position.

4. The electronic endoscope system according to claim 2, wherein the noise suppressor includes a band elimination filter that obtains a frequency band corresponding to the noise cycle based on the noise cycle and the cycle length and eliminates the noise component from the echo signal by using the frequency band.

5. The electronic endoscope system according to claim 1, wherein the noise suppressor performs correction processing of replacing a pixel value of the detected noise component at a noise pixel position in the ultrasonic image with an interpolation pixel value generated based on pixel values of peripheral pixels positioned around the noise pixel position.

6. The electronic endoscope system according to claim 1, wherein the noise suppressor changes at least one of operation frequencies of a plurality of component devices included in the captured image processor and the ultrasonic image processor so as to be separated from a generation cycle of the noise component periodically generated in the echo signal.

7. The electronic endoscope system according to claim 6, wherein the operation frequencies include at least one of an ultrasonic frequency of the ultrasound probe or an image sensor operation frequency of the image sensor.

8. The electronic endoscope system according to claim 6, wherein the ultrasonic image processor includes, as the component device, an A/D converter that converts the echo signal, which is an analog signal, into a digital signal by sampling, and
   the operation frequencies include a sampling frequency of the echo signal in the A/D converter.

9. The electronic endoscope system according to claim 6, wherein the ultrasonic image processor includes, as the component device, a DC/DC converter that is a switching power supply for driving the electronic endoscope, the captured image processor, and the ultrasonic image processor, and
   the operation frequencies include a switching frequency in the DC/DC converter.

10. The electronic endoscope system according to claim 9, wherein the ultrasonic image processor includes, as the component device, an AC/DC converter which is a switching power supply that converts AC power received from an external commercial power supply into DC power and supplies the DC power to the DC/DC converter, and
    the operation frequencies include a switching frequency in the AC/DC converter.

11. The electronic endoscope system according to claim 10, wherein the DC/DC converter and the AC/DC converter include a storage battery that supplies DC power, and
    the suppressor performs switching from the DC/DC converter and the AC/DC converter to the storage battery when the noise component is detected.

12. The electronic endoscope system according to claim 1, further comprising an electronic endoscope position measurement device that specifies a position of the electronic endoscope by using magnetism when the electronic endoscope is inserted into a body cavity, wherein
    the electronic endoscope position measurement device includes a driver of a transmission coil wound around the electronic endoscope, and a position specifier that specifies the position of the electronic endoscope by using a signal from the transmission coil when the electronic endoscope is inserted into the body cavity, and
    the noise suppressor changes an operation frequency of the transmission coil to be generated or stops generation of the magnetism when the noise component is detected.

13. The electronic endoscope system according to claim 1, wherein the noise detector:
    creates a noise component inference model that has learned, by machine learning, a presence or absence of the noise component in advance by using, as training data, a training ultrasonic image without the noise component and a training ultrasonic image with the noise component, and determines the presence or absence of the noise component by inputting the ultrasonic image generated by the ultrasonic image processor to the noise component inference model.

14. The electronic endoscope system according to claim 13, wherein the noise suppressor creates a noise control inference model that has learned, by machine learning, a relationship between: operation environment information of the electronic endoscope, the captured image processor, or the ultrasonic image processor and a feature amount of the ultrasonic image; and information regarding whether a countermeasure for suppressing the noise component is effective or ineffective according to the operation environment information, and sets a countermeasure effective for suppressing the noise by extracting the feature amount of the ultrasonic image when the noise component is detected in a newly generated ultrasonic image by the noise detector, and inputting, to the created noise control inference model, the operation environment information and the extracted feature amount when the noise component is detected.

15. The electronic endoscope system according to claim 14, wherein the operation environment information includes operation frequencies of a plurality of component devices included in the captured image processor and the ultrasonic image processor, and the operation frequencies include an ultrasonic frequency of the ultrasound probe and an operation frequency of the image sensor, a sampling frequency of the echo signal in an A/D converter, a switching frequency in a DC/DC converter and an AC/DC converter, and an operation frequency of a transmission coil of an electronic endoscope position measurement device.

16. The electronic endoscope system according to claim 1, further comprising a display that outputs an ultrasonic image, the ultrasonic image including the suppressed detected noise component.

* * * * *